United States Patent
Bacino et al.

(10) Patent No.: US 9,730,726 B2
(45) Date of Patent: Aug. 15, 2017

(54) BALLOON ASSEMBLIES HAVING CONTROLLABLY VARIABLE TOPOGRAPHIES

(71) Applicant: W. L. Gore & Associates, Inc., Newark, DE (US)

(72) Inventors: John E. Bacino, Landenberg, PA (US); Carey V. Campbell, Flagstaff, AZ (US); Edward H. Cully, Flagstaff, AZ (US); Jeffrey B. Duncan, Flagstaff, AZ (US); Douglas S. Paget, Flagstaff, AZ (US); John M. Squeri, Downingtown, PA (US); Benjamin M. Trapp, Flagstaff, AZ (US); Michael J. Vonesh, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 659 days.

(21) Appl. No.: 13/645,414

(22) Filed: Oct. 4, 2012

(65) Prior Publication Data

US 2013/0116655 A1    May 9, 2013

Related U.S. Application Data

(60) Provisional application No. 61/545,039, filed on Oct. 7, 2011.

(51) Int. Cl.
*A61M 25/10*    (2013.01)
*A61B 17/3207*    (2006.01)

(52) U.S. Cl.
CPC . *A61B 17/320725* (2013.01); *A61M 25/1002* (2013.01); *A61M 25/104* (2013.01);
(Continued)

(58) Field of Classification Search
CPC .......... A61M 25/1002; A61M 25/1018; A61M 25/104; A61M 25/1027; A61M 2025/105;
(Continued)

(56) References Cited

U.S. PATENT DOCUMENTS

| 4,771,776 A | 9/1988 | Powell et al. |
| 4,941,877 A | 7/1990 | Montano |

(Continued)

FOREIGN PATENT DOCUMENTS

| DE | 19952505 | 5/2001 |
| EP | 0808613 | 11/1997 |

(Continued)

OTHER PUBLICATIONS

International Search Report and Written Opinion for PCT/US2012/059024 mailed Feb. 6, 2013, corresponding to U.S. Appl. No. 13/645,414.

(Continued)

*Primary Examiner* — Nathan R Price
*Assistant Examiner* — Justin L Zamory
(74) *Attorney, Agent, or Firm* — Kilpatrick Townsend & Stockton, LLP

(57) ABSTRACT

Various embodiments provide a device comprising a balloon disposed at least partially along a template, the template including an aperture, wherein the template has a substantially cylindrical portion that resists deformation in a radial direction, wherein the balloon expands radially during inflation, wherein a portion of the balloon at least partially protrudes about the aperture. Other embodiments are directed toward balloons having textured surfaces.

20 Claims, 30 Drawing Sheets

(52) U.S. Cl.
CPC .... *A61M 25/1027* (2013.01); *A61M 25/1029* (2013.01); *A61M 25/10184* (2013.11); *A61M 2025/105* (2013.01); *A61M 2025/1031* (2013.01); *A61M 2025/1059* (2013.01); *A61M 2025/1084* (2013.01); *A61M 2025/1086* (2013.01); *Y10T 29/49826* (2015.01); *Y10T 29/49888* (2015.01)

(58) Field of Classification Search
CPC .. A61M 2025/1072; A61M 2025/1059; A61M 2025/1084; A61M 2025/1031; A61M 2025/1086; A61M 2025/1075; A61M 2025/1081; A61M 2025/1088; A61M 2025/109; A61B 17/320725

See application file for complete search history.

(56) References Cited

U.S. PATENT DOCUMENTS

| | | |
|---|---|---|
| 4,950,232 A | 8/1990 | Ruzicka et al. |
| 5,250,070 A | 10/1993 | Parodi |
| 5,334,148 A | 8/1994 | Martin |
| 5,409,458 A | 4/1995 | Khairkhahan et al. |
| 5,476,589 A | 12/1995 | Bacino |
| 5,484,411 A | 1/1996 | Inderbitzen et al. |
| 5,487,730 A | 1/1996 | Marcadis et al. |
| 5,545,132 A | 8/1996 | Fagan et al. |
| 5,620,457 A | 4/1997 | Pinchasik et al. |
| 5,693,014 A | 12/1997 | Abele et al. |
| 5,708,044 A | 1/1998 | Branca |
| 5,746,968 A | 5/1998 | Radisch, Jr. |
| 5,759,172 A | 6/1998 | Weber et al. |
| 5,913,871 A | 6/1999 | Werneth et al. |
| 5,954,740 A | 9/1999 | Ravenscroft et al. |
| 5,954,745 A | 9/1999 | Gertler et al. |
| 6,007,545 A | 12/1999 | Venturelli |
| 6,022,359 A | 2/2000 | Frantzen |
| 6,039,757 A | 3/2000 | Edwards et al. |
| 6,048,332 A | 4/2000 | Duffy et al. |
| 6,120,477 A | 9/2000 | Campbell et al. |
| 6,129,706 A | 10/2000 | Janacek |
| 6,245,040 B1 | 6/2001 | Inderbitzen et al. |
| 6,478,807 B1 | 11/2002 | Foreman et al. |
| 6,527,739 B1 | 3/2003 | Bigus et al. |
| 6,541,589 B1 | 4/2003 | Baillie |
| 6,676,667 B2 | 1/2004 | Marerio et al. |
| 6,736,841 B2 | 5/2004 | Musbach et al. |
| 6,814,730 B2 | 11/2004 | Li |
| 6,835,189 B2 | 12/2004 | Musbach et al. |
| 6,841,213 B2 | 1/2005 | Parsonage et al. |
| 6,875,197 B1 | 4/2005 | Simhambhatla et al. |
| 6,942,680 B2 | 9/2005 | Grayzel et al. |
| 6,989,025 B2 | 1/2006 | Burgmeier et al. |
| 6,991,617 B2 | 1/2006 | Hektner et al. |
| 7,004,963 B2 | 2/2006 | Wang et al. |
| 7,008,438 B2 | 3/2006 | O'Brien |
| 7,049,380 B1 | 5/2006 | Chang et al. |
| 7,083,639 B2 | 8/2006 | Guinan et al. |
| 7,195,638 B1 | 3/2007 | Sridharan |
| 7,273,471 B1 | 9/2007 | Wang et al. |
| 7,303,572 B2 | 12/2007 | Melsheimer et al. |
| 7,306,616 B2 | 12/2007 | Eidenschink et al. |
| 7,335,184 B2 | 2/2008 | Laguna |
| 7,531,611 B2 | 5/2009 | Sabol et al. |
| 7,572,270 B2 | 8/2009 | Johnson |
| 7,686,824 B2 | 3/2010 | Konstantino et al. |
| 7,927,362 B2 | 4/2011 | Shippy, III et al. |
| 7,976,497 B2 | 7/2011 | Shah et al. |
| 8,048,028 B2 | 11/2011 | Horn et al. |
| 8,048,093 B2 | 11/2011 | Mapes et al. |
| 8,048,440 B2 | 11/2011 | Chang et al. |
| 8,083,761 B2 | 12/2011 | Meens |
| 8,216,267 B2 | 7/2012 | Pallazza |
| 8,221,484 B2 | 7/2012 | Wesselmann |
| 8,292,912 B2 | 10/2012 | Burton et al. |
| 8,637,144 B2 | 1/2014 | Ford |
| 9,139,669 B2 | 9/2015 | Xu et al. |
| 2001/0035456 A1 | 11/2001 | Lennox |
| 2002/0010489 A1* | 1/2002 | Grayzel .................. A61F 2/958 606/194 |
| 2002/0045914 A1 | 4/2002 | Roberts et al. |
| 2002/0161388 A1* | 10/2002 | Samuels et al. .............. 606/192 |
| 2003/0032999 A1 | 2/2003 | Huang |
| 2004/0122508 A1 | 6/2004 | White et al. |
| 2005/0137621 A1 | 6/2005 | Stahl et al. |
| 2005/0149082 A1* | 7/2005 | Yee et al. .................... 606/159 |
| 2005/0216047 A1 | 9/2005 | Kumoyama et al. |
| 2006/0136032 A1 | 6/2006 | Legarda et al. |
| 2006/0178685 A1 | 8/2006 | Melsheimer |
| 2007/0061006 A1 | 3/2007 | Desatnik et al. |
| 2007/0088323 A1* | 4/2007 | Campbell et al. ............ 604/523 |
| 2007/0106216 A1* | 5/2007 | Noddin .................... 604/103.09 |
| 2008/0065188 A1 | 3/2008 | Pallazza |
| 2008/0097301 A1* | 4/2008 | Alpini et al. ............. 604/103.07 |
| 2008/0147103 A1 | 6/2008 | Shekalim |
| 2009/0124969 A1 | 5/2009 | Lenz |
| 2009/0192453 A1* | 7/2009 | Wesselmann ............. 604/101.01 |
| 2009/0281490 A1 | 11/2009 | McAuley et al. |
| 2009/0281564 A1 | 11/2009 | Kontos |
| 2009/0283206 A1 | 11/2009 | Eskaros et al. |
| 2009/0299450 A1 | 12/2009 | Johnson et al. |
| 2010/0036314 A1 | 2/2010 | Burton et al. |
| 2010/0042198 A1 | 2/2010 | Burton |
| 2010/0094209 A1 | 4/2010 | Drasler et al. |
| 2010/0189876 A1* | 7/2010 | Kokish et al. ................. 427/2.3 |
| 2010/0312182 A1 | 12/2010 | Adden et al. |
| 2011/0046711 A1 | 2/2011 | Degen et al. |
| 2011/0152683 A1 | 6/2011 | Gerrans et al. |
| 2011/0172598 A1 | 7/2011 | Sampognaro et al. |
| 2011/0230946 A1 | 9/2011 | Butcher et al. |
| 2012/0059401 A1* | 3/2012 | Konstantino ........... A61F 2/958 606/159 |
| 2012/0083733 A1 | 4/2012 | Chappa |

FOREIGN PATENT DOCUMENTS

| | | |
|---|---|---|
| EP | 0872253 | 10/1998 |
| EP | 1 338 300 | 8/2003 |
| EP | 1 683 541 | 7/2006 |
| EP | 1 892 007 | 2/2008 |
| EP | 2 431 067 | 3/2012 |
| GB | 1327858 | 8/1973 |
| JP | 1990-174849 | 7/1990 |
| JP | 1996-052219 | 2/1996 |
| JP | 1999-319103 | 11/1999 |
| JP | 2002-045435 | 2/2002 |
| JP | 2005-349202 | 12/2005 |
| JP | 2007-502687 | 2/2007 |
| JP | 2009-540918 | 11/2009 |
| JP | 2011-513005 | 4/2011 |
| WO | 87/01600 | 3/1987 |
| WO | 97/10871 | 3/1997 |
| WO | 97/17889 | 5/1997 |
| WO | 0145781 | 6/2001 |
| WO | 2007/095705 | 8/2007 |
| WO | 2008/021003 | 2/2008 |
| WO | 2011/112863 | 9/2011 |
| WO | 2012/142540 | 10/2012 |
| WO | 2013/009740 | 1/2013 |

OTHER PUBLICATIONS

International Search Report and Written Opinion for PCT/US2014/027615 mailed Sep. 15, 2014, corresponding to U.S. Appl. No. 14/209,711; 7 pages.

Annex to Form PCT/ISA/206 Communication Relating to the Results of the Partial International Search Report and Written Opinion for PCT/US2012/059024 mailed Dec. 17, 2012, corresponding to U.S. Appl. No. 13/645,414.

GRIP™ by Acrostak—Product Specification Sheet and Brochure.

Gurbel PA, Anderson RD, Peels HO, van Boven AJ, den Heijer P.

(56) References Cited

OTHER PUBLICATIONS

Coronary Artery Angioplasty with a Helical Autoperfusion Balloon Catheter. Catheterization and Cardiovascular Diagnosis (Online) Feb. 1997, 40(2); 179-185. (Abstract).
Hosokawa Y, Tanaka K, Mizuno K. Successful Treatment for Refractory Coronary Thrombus with Scoring Balloon Angioplasty. Catheterization and Cardiovascular Interventions (Online) 2012, 79:282-287.

* cited by examiner

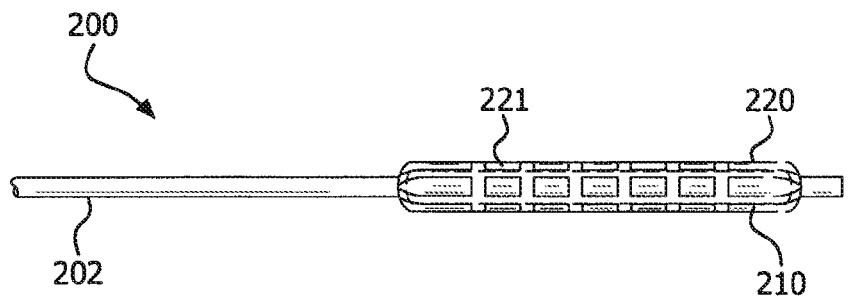
FIG. 2B(1)
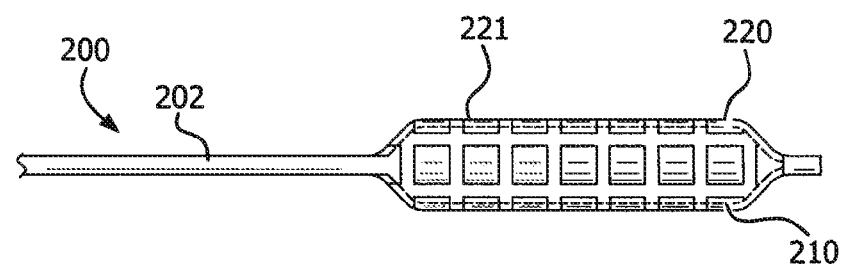
FIG. 2B(2)
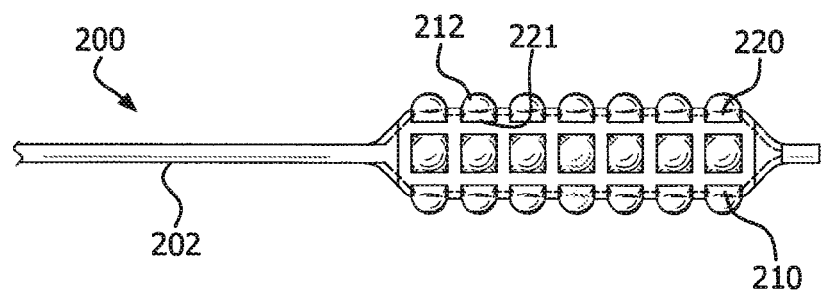
FIG. 2B(3)

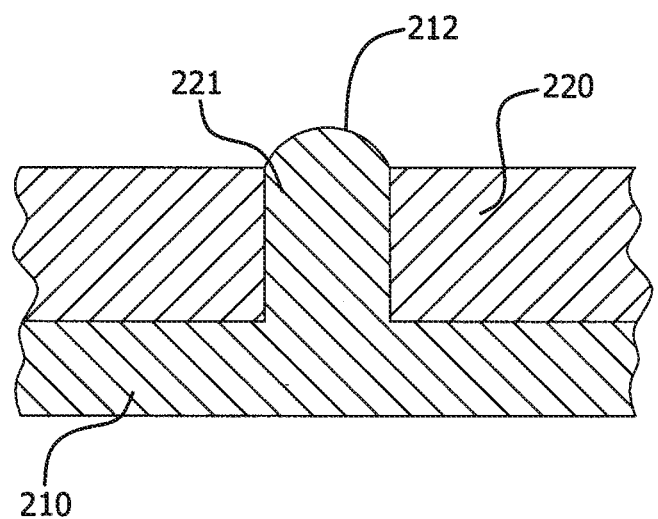
FIG. 2B (4)

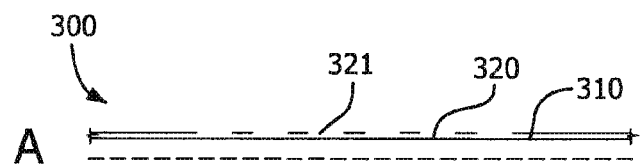
FIG. 3A (1)
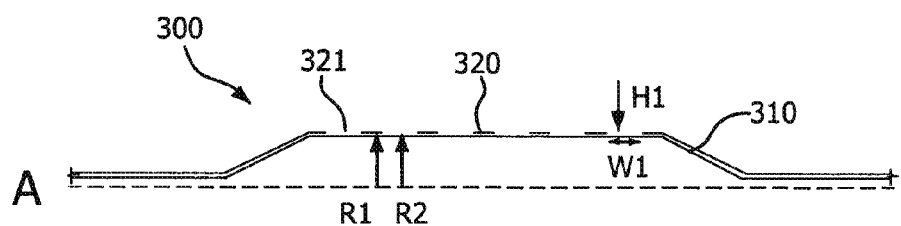
FIG. 3A (2)
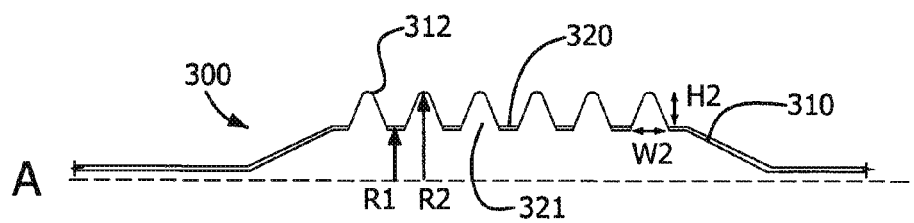
FIG. 3A (3)

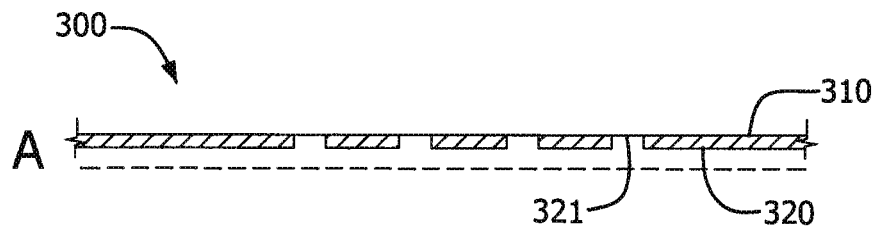
FIG. 3B (1)
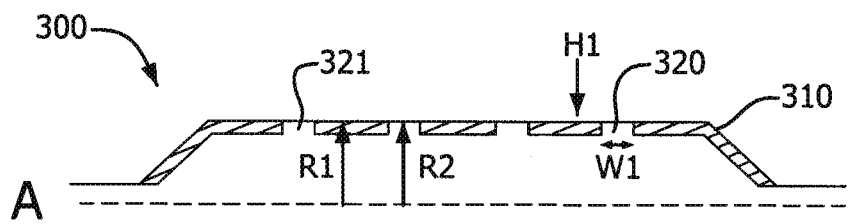
FIG. 3B (2)
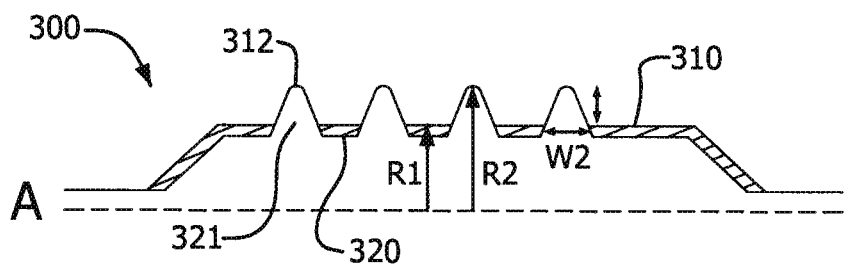
FIG. 3B (3)

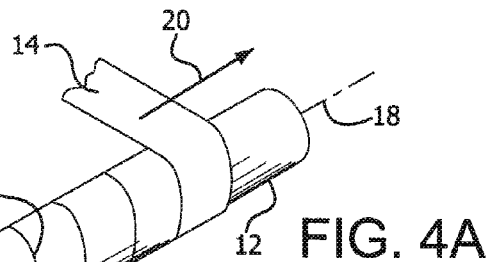
FIG. 4A
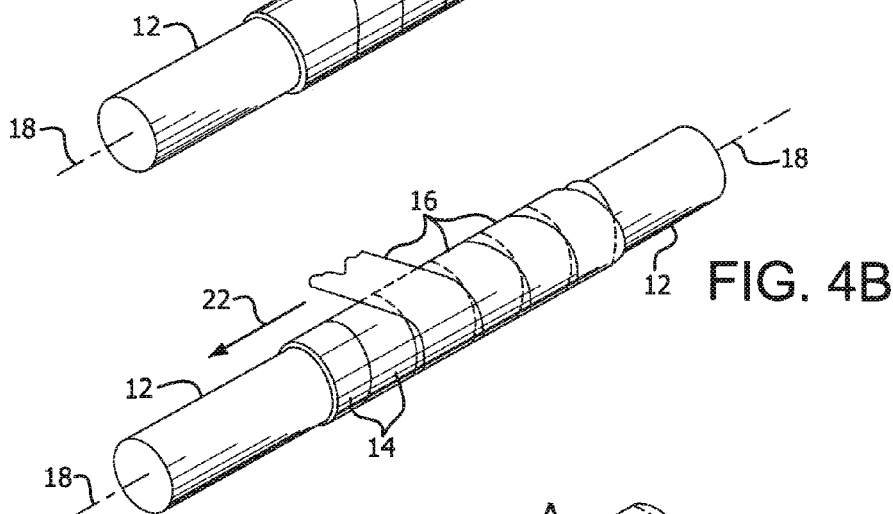
FIG. 4B
FIG. 4C
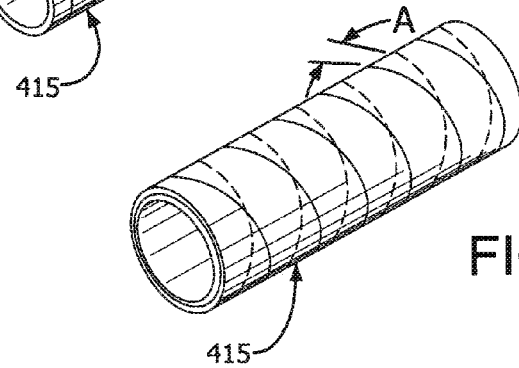
FIG. 4D

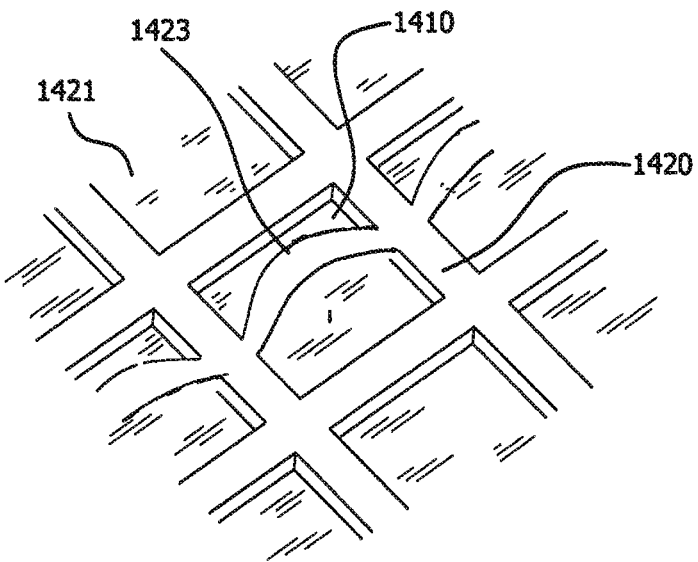
FIG. 14C(1)
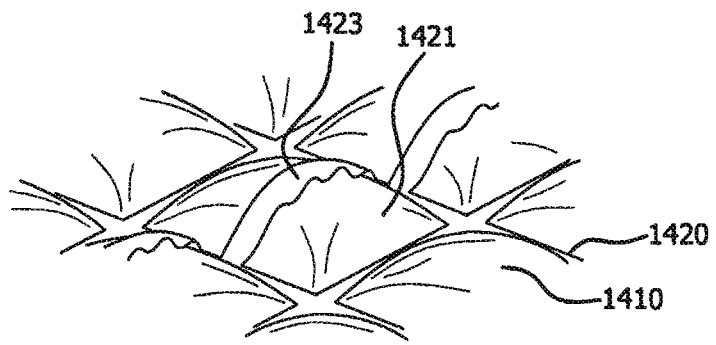
FIG. 14C(2)
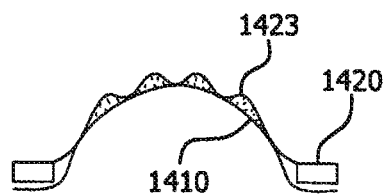
FIG. 14C(3)

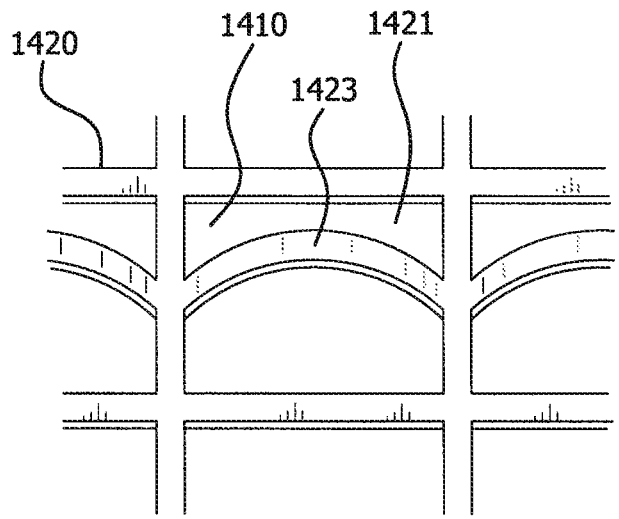
FIG. 14D(1)
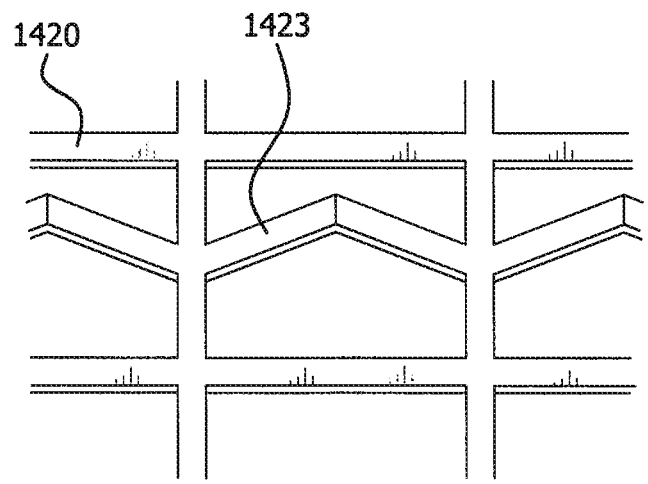
FIG. 14D(2)

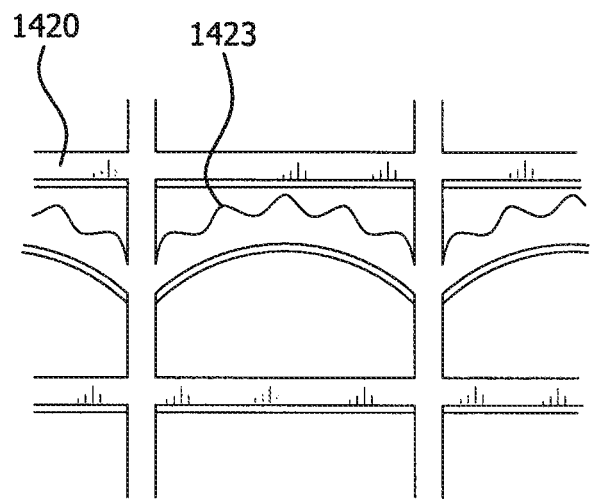
FIG. 14D(3)
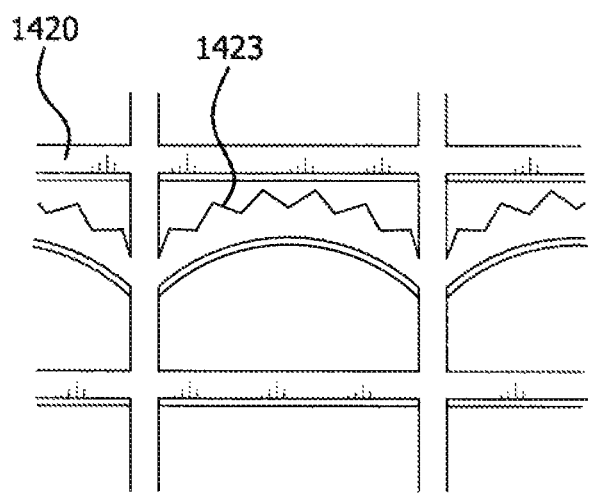
FIG. 14D(4)

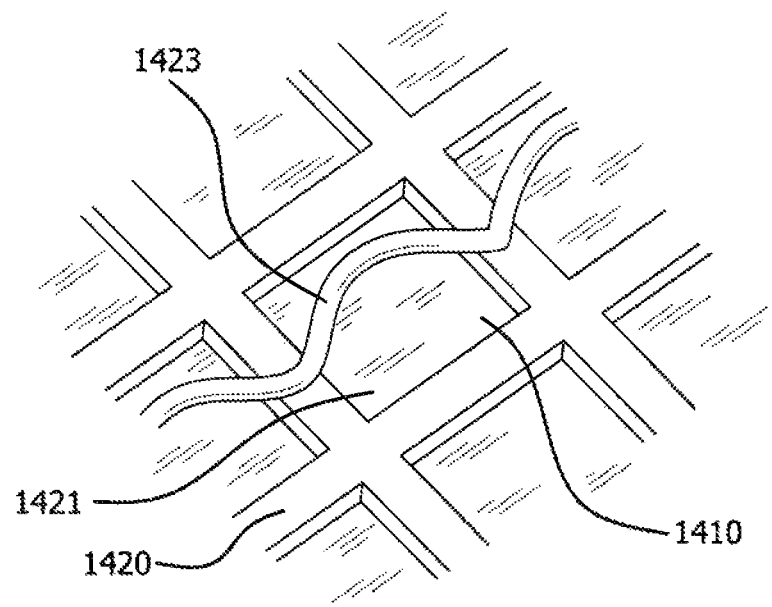
FIG. 14E(1)
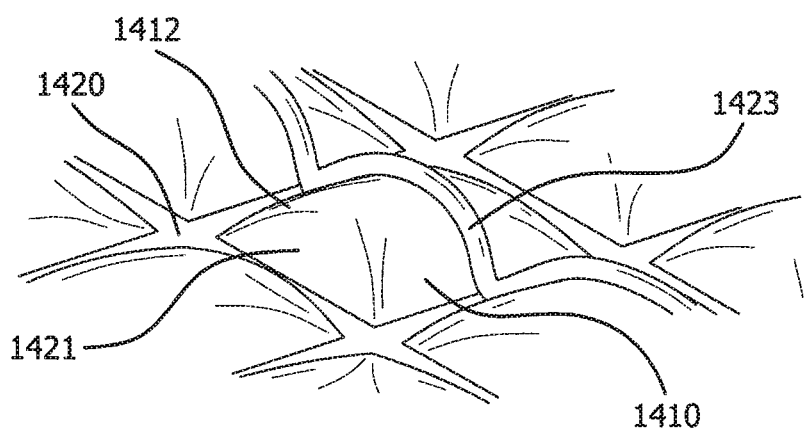
FIG. 14E(2)

BALLOON ASSEMBLIES HAVING CONTROLLABLY VARIABLE TOPOGRAPHIES

CROSS-REFERENCE TO RELATED APPLICATION

This application is a non-provisional of and claims priority to U.S. Provisional No. 61/545,039, filed on Oct. 7, 2011 and entitled "Balloon Assemblies having Controllably Variable Topographies", wherein such provisional application is hereby incorporated by reference in its entirety.

BACKGROUND OF THE DISCLOSURE

Field of the Disclosure

The present disclosure relates generally to balloon assemblies having controllable topographies and systems and methods relating to the same.

Discussion of the Related Art

Balloons intended for use within a mammalian body, such as a human, are employed in a variety of medical procedures, including dilation of narrowed blood vessels, placement of stents and other implantable devices, temporary or permanent occlusion of blood vessels, drug delivery, thrombectomy, embolectomy, atherectomy, angioplasty, other endovascular procedures, and other procedures within a lumen of a mammalian body such as a human body. In this regard, as used herein, the term "body" can comprise a mammalian body such as a human body or other animal body.

In a typical application, a balloon (often coupled with a catheter) is advanced to the desired location in the vascular system or other lumen of the body. The balloon is then pressure-expanded in accordance with a medical procedure. Thereafter, the pressure is removed from the balloon, allowing the balloon to contract and permit removal of the catheter and, in many cases, the balloon.

Procedures such as these are generally considered minimally invasive, and are often performed in a manner which minimizes disruption to the patient's body. As a result, balloons are often inserted from a location remote from the region to be treated. For example, during angioplasty procedures involving coronary vessels, the balloon catheter is typically inserted into the femoral artery in the groin region of the patient, and then advanced through vessels into the coronary region of the patient. These balloons typically include some type of radiopaque marker to allow the physician performing the procedure to monitor the progress of the catheter through the body.

Non-compliant balloons are generally made of relatively strong but generally inelastic material (e.g., nylon, polyester, etc.), which must be folded to obtain a compact, small diameter cross section for delivery. These relatively stiff balloons do not easily conform to the surrounding vessel and thus can be used to compact hard deposits in vessels. Due to the need for strength and stiffness, these devices are rated to employ high inflation pressures, usually up to about 4 to about 60 atmospheres. As depicted in FIG. 1, non-compliant balloons (line C) have a maximum diameter, and as inflation fluid is introduced, such balloons will not normally distend appreciably beyond a maximum diameter. Once a non-compliant balloon is inflated to its maximum diameter, the exertion of additional pressure can cause rupture of the balloon, creating a hazardous condition.

By contrast, compliant balloons generally comprise soft, elastic material (e.g., natural rubber latex). As depicted in FIG. 1, compliant balloons (line A) will generally expand continuously in diameter and will not appreciably increase in internal pressure as inflation fluid is introduced. As a result, compliant balloons are generally rated by volume (e.g., 0.3 cc) rather than by nominal diameter. Also, compliant balloons generally conform to the shape of the vessel. Although comparatively weak compared to non-compliant balloons, compliant balloons have the advantage that they need not be folded about a delivery catheter (reducing profile) and tend to readily recompact to their initial size and dimensions following inflation and subsequent deflation. These balloons can be employed to displace soft deposits, such as a thrombus, where a soft and tacky material such as latex provides an effective extraction means, and also can be used as an occlusion balloon, operating at low pressures.

In between the spectrum of compliant balloons and non-compliant balloons fall semi-compliant balloons. As depicted in FIG. 1, semi-compliant balloons (line B) will both increase in pressure and increase in diameter as inflation fluid is introduced. However, semi-compliant balloons operate at pressures in between the two types of balloons and will continue to distend as inflation fluid is introduced.

Both compliant and non-compliant balloons tend to have a uniform surface topography. In other words, conventional balloons tend to have smooth surfaces. Balloons with more varied topographies may facilitate a variety of medical procedures and therapies not possible using conventional balloons. For instance, a variable topography may provide increased surface area over a similar conventional balloon, and thus interaction with the body may be improved. A variable topography balloon may also be configured to deploy sharp objects in a localized, difficult to reach part of the body, providing an improvement in therapy. In addition, variable topography balloons may provide improved drug delivery systems. Moreover, it would be beneficial for a balloon to have a controllable topography.

SUMMARY OF THE DISCLOSURE

The present disclosure provides systems and methods for balloon assemblies having varied topographies and preconfigured surface textures. In various embodiments, a device is provided comprising a balloon comprising a size limiting layer and a template disposed around or within the balloon. The template comprises at least one aperture and a portion that is more resistant to deformation in a radial direction than the balloon or the size limiting layer, either because template comprises a less compliant material or has an upper distension limit that is less than the size limiting layer's upper distension limit. As such, the balloon and size limiting layer are configured to distend beyond the template about the aperture at a given volume/pressure. The balloon and size limiting layer will distend about an aperture to a second inflated state comprising a varied topography. The size limiting layer prevents further appreciable distension beyond the second inflated state. In various embodiments, the template and/or balloon can optionally comprise an expanded polytetrafluoroethylene (ePTFE). The balloon and/or template can comprise a tape wrapped membrane. Other embodiments comprise methods of making and using the same.

In various embodiments, a balloon assembly is provided comprising a balloon having a controlled topography, wherein the balloon assembly has a smooth or substantially wrinkle free surface at a first inflated state and a varied topography surface at a second inflated state. In an embodiment wherein the balloon assembly comprises an inner balloon and an outer template, the inner diameter of the template at a first inflated state is substantially equal to the outer diameter of the balloon at a first inflated state. In an embodiment wherein an outer balloon is disposed around an inner template, the converse is true; namely, the outer diameter of the template at a first inflated state is substantially equal to the inner diameter of the balloon in the first inflated state. The balloon and/or template can comprise a tape wrapped membrane. Other embodiments comprise methods of making and using the same.

In other embodiments, a balloon assembly can comprise an underlying compliant balloon and an overlying less compliant template having at least one aperture. Located within the aperture can be a therapeutic agent, preferably in a solid or viscous form. Upon inflation, the underlying compliant balloon will protrude through the aperture and convey the therapeutic agent external to the template. In this manner, a therapeutic agent can be delivered to a surrounding tissue such as the intima of a vessel. Other embodiments include methods of making and using the same.

Another aspect of the present disclosure comprises textured balloon assemblies. In various embodiments, a balloon can be covered and/or wrapped with a textured network that provides a topographical feature. For example, a textured network can comprise beads, filaments, fibers, rings, knits, weaves, and/or braids, which can be wrapped or otherwise disposed over or within a balloon. The textured network creates raised surface patterns that can provide therapeutic effect. Other embodiments include methods of making and using the same.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the disclosure.

FIGS. 2B(1) to 2B(3) illustrates a varied topography balloon assembly embodiment of the present disclosure in a deflated state; a first inflated state; and a second inflated state;

FIG. 2B(4) illustrates a close up, cross-sectional view about an aperture of a varied topography balloon assembly embodiment illustrated in FIG. 2B(3);

FIGS. 3A(1) to 3A(3) schematically illustrate the process under which various embodiments distend to a second inflated state thereby forming a varied topography balloon assembly;

FIGS. 3B(1) to 3B(3) schematically illustrate the process under which various embodiments distend to a second inflated state thereby forming a varied topography balloon assembly;

FIGS. 4A to 4D illustrate wrapping a film tape to form a size limiting membrane layer;

FIG. 14C(1) illustrates a close-up, perspective view of a deflated balloon assembly with an arced element across the aperture of a template, in accordance with various embodiments;

FIG. 14C(2) illustrates a close-up, perspective view of an inflated balloon assembly with a deployed arced element across the aperture of a template, in accordance with various embodiments; (C3)

FIG. 14D(1) to 14D(4) illustrate the various patterns of template comprising an arced element across the aperture; (E1-2)

DETAILED DESCRIPTION OF THE ILLUSTRATED EMBODIMENTS

Figure 1:
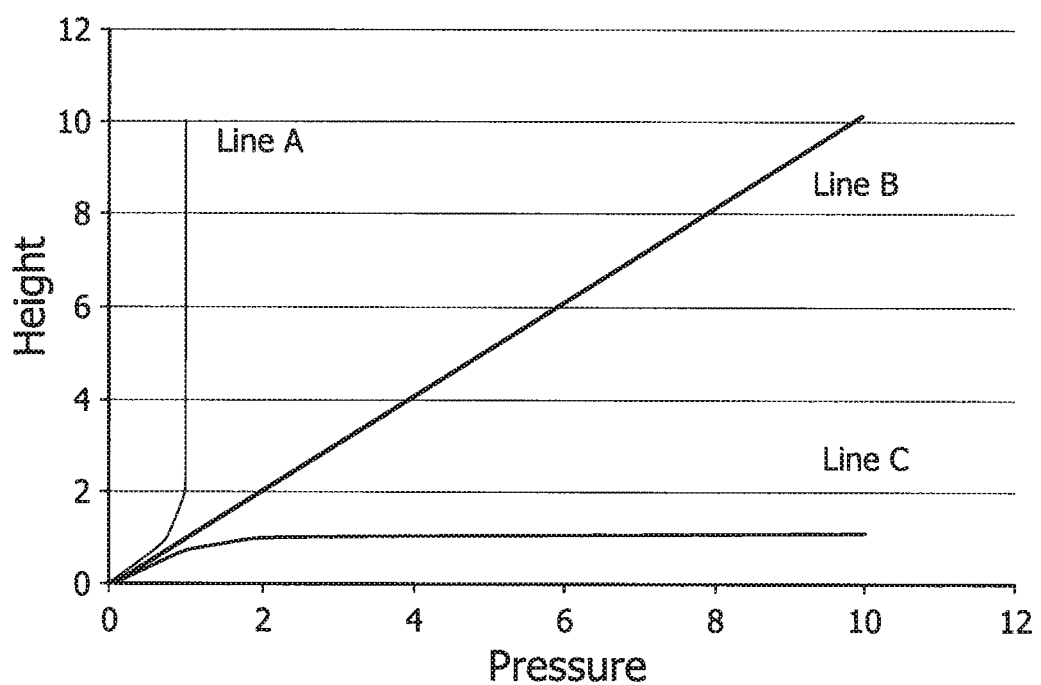
FIG. 1 compares pressure to height of complaint balloons (Line A), semi-compliant balloons (Line B), and non-compliant balloons (Line C)

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

As used herein, "balloon assembly" means a balloon coupled with one or more other components, such as a template (described herein), size limiting layer (descried herein), catheter, distal cap ("olive"), cover, or other apparatus.

As used herein, the term "size limiting" means that a material or component has an upper distension or deformation limit beyond which a material or component will not appreciably expand, distend, and/or deform. For example, a size-limited balloon can be inflated to a maximum diameter, and once this diameter is reached, further increases in pressure will not cause an appreciable increase in its diameter. As reflected in FIG. 1, a non-compliant balloon (line C) is a size-limited balloon, and traditional compliant (line A) and semi-compliant (line B) balloons are not size-limited balloons. Accordingly, a "compliant balloon," as used herein, refers to both compliant and semi-compliant balloons or balloons that are not size limited, but will continue to expand, distend, and/or deform as the internal pressure increases until the point of failure, e.g., the balloon wall ruptures. In accordance with certain embodiments of the present disclosure, the described "compliant" balloons are referred to as such because the described balloons generally conform to the shape of their surroundings (e.g., a surrounding anatomy or vessel) like traditional "compliant" balloons, e.g., portions of the described "compliant" balloons are able to outwardly extend from the template to form protrusions.

As used herein, the term "to inflate" can mean to fill or cause expansion by introducing a flowable substance (e.g., an influx of fluid), such as a liquid (e.g., saline), a gel, or a gas.

As used herein, the term "inflated" means a balloon at an internal pressure or volume above the internal pressure or volume at which the balloon begins to expand from a deflated state. As used herein, a "first inflated state" refers to an inflated balloon at a first pressure or first volume which will result in a balloon with a generally smooth or uniform surface, except perhaps with respect to slight recesses at the site of the aperture(s). As used herein, a "second inflated state" refers to an inflated balloon at a second pressure or second volume greater than the first pressure or first volume which will result in a balloon with a varied topography. As used herein, "varied topography" refers to a balloon assembly surface that has textured, bumpy, ribbed, or other three-dimensional surfaces.

As used herein, the term "elongate element" is generally any element configured for relative axial movement with an endoluminal device delivery element (e.g., a catheter-based endoluminal device delivery element such as a balloon catheter) and includes any longitudinally extending structure with or without a lumen therethrough. Thus, elongate elements include but are not limited to tubes with lumens (e.g., catheters), solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Elongate elements can be any material and can have any cross-sectional shape including, but not limited to, profiles that are elliptical, non-elliptical, or random.

As described herein, balloon assemblies used inside the body generally interact with the body through contact with an exterior surface of the balloon assembly. Thus, the surface topography of a balloon assembly can affect the physical interaction between the balloon assembly and the body or a device inside the body. The ability to control a balloon's topography, or three dimensional surface characteristics, allows balloon assemblies to interact with the body in new or improved modes. Various advantages can be realized using controllably variable topography balloon assemblies. For example, balloon assemblies, such as those that can be used with a catheter, can be inserted into a lumen of the body. The balloon assembly can interact with the body in a variety of ways which can be facilitated by designing topographies which yield improved results. In this regard, for example, a balloon having a varied topography can improve engagement with a vessel wall and/or improve atherosclerotic plaque or thrombus removal ability, such from a vessel wall or the wall of an endoprosthesis.

Figure 2A:
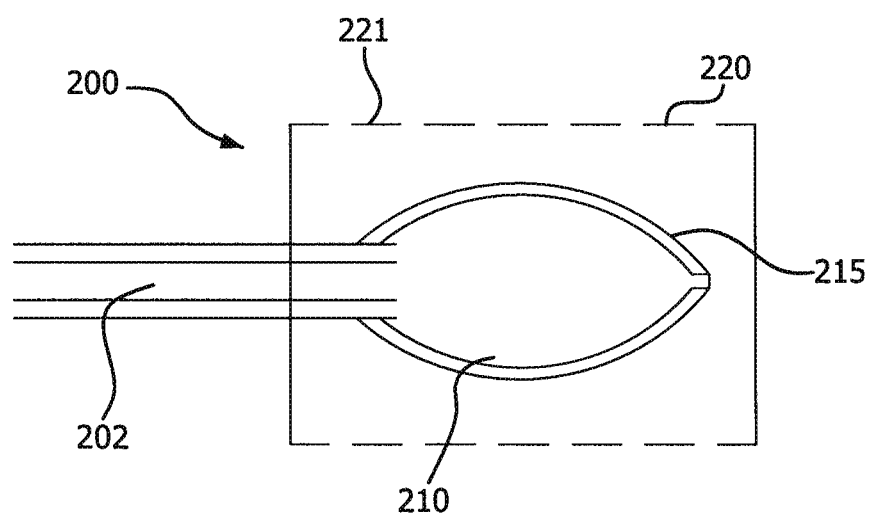
FIG. 2A illustrates a schematic varied topography balloon assembly embodiment from a cross-sectional perspective.

By selectively constraining the expansion of a balloon at selected sites, the balloon assembly topography can be varied. For example, with reference to FIG. 2A, a schematic of a balloon assembly 200 is shown. FIGS. 2B(1) to 2B(3) illustrate a varied topography balloon 200 in a deflated state (FIG. 2B(1)), a first inflated state having a generally uniform or smooth surface (FIG. 2B(2)), and a second inflated state having a varied topography (FIG. 2B(3)). FIG. 2B(4) illustrates a close-up, cross-sectional view of a protrusion 212 of a varied topography balloon 200.

Balloon assembly 200 comprises balloon 210 and template 220. Balloon 210 can be disposed along template 220, either underlying or overlying the template 220. The balloon 210 may comprise a working length and at least one tapered section (i.e., a shoulder). The template 220 may extend along at least a portion of the working length of the balloon 210. The template 220 may also extend along at least a portion of at least one shoulder of the balloon 210. Assembly 200 can further comprise a catheter 202 to which balloon 210 and template 220 are attached. Catheter 202 is shown in fluid communication with balloon 210, such that fluid can be introduced through catheter 202 into balloon 210. Catheter 202 can be coupled to any suitable medical device, such as a syringe, an indeflator, pump or any other apparatus for conducting fluid through catheter 202 and into balloon 210.

Template 220 can be an overlying or underlying structure comprising at least one aperture 221. Template 220 constrains a portion of balloon 210 during inflation. In this regard, balloon 210 is inflated to a second inflated state, and the restraining action of template 220 causes balloon 210 to distend at apertures 221 in template 220 as described in more detail below.

The operation of the balloon assemblies of the present disclosure is shown schematically for various embodiments in FIGS. 3A(1) to 3A(3) and 3B(1) to 3B(3) in which is illustrated a longitudinal cross section of a balloon assembly 300. In FIGS. 3A(1) to 3A(3), balloon 310 underlies template 320 which features apertures 321. In FIGS. 3B(1) to 3B(3), balloon 310 overlies template 320, and template 320 adheres to balloon during inflation. In these illustrations, balloon 310 and template 320 are shown aligned with axis "A". Axis "A" can comprise the longitudinal axis of a catheter.

A first inflated state is shown in FIGS. 3A(2) and 3B(2). With reference to FIG. 3A(2), balloon 310 has an outer radius shown as "R1" under template 320, and template 320 has an inner radius of "R2". With reference to FIG. 3B(2), balloon 310 has an inner radius shown as "R1" over template 320, and template 320 has an outer radius "R2". In the first inflated state, radius "R1" is substantially equal to radius "R2". No protrusions are observed in a first inflated state. Stated differently, the height, "H1" of balloon material or protrusions above template 320 has a value of zero or close to zero. At the first inflated state, balloon 310 comprises a substantially smooth or wrinkle free surface. Also in the first inflated state, aperture 321 has a width shown as "W1" in the figures.

FIGS. 3A(3) and 3B(3) depict balloon assembly 300 in a second inflated state. As balloon 110 is inflated beyond a first inflated state, radius "R2" increases relative to radius "R1" about aperture 321. This is because balloon 310, upon distention, begins to distend about or protrude from or above apertures 321. Radius "R1" remains essentially at the same dimension as in the first inflated state shown FIGS. 3A(2) and 3B(2). In some embodiments, width of aperture 321 ("W2") remains close to or even equal to width of aperture 221 ("W1") in the previous inflated state shown in FIGS. 3A(2) and 3B(2). In other embodiments, W2 can be greater than W1; i.e., aperture 320 can increase in size as balloon assembly 300 is inflated. It will be understood that radius "R2" can be a maxima, in particular if a size limiting layer or a size limited balloon is used as described below.

Referring again to FIGS. 2A and 2B(1) to 2B(4), in various embodiments, balloon 210 can comprise any suitable compliant balloon. As described above, a compliant balloon can comprise a polymeric material. Exemplary materials for a compliant balloon include elastomers such as polyurethane and silicone, natural rubber or latex products, synthetic rubber such as nitrile butadiene, or other synthetic or naturally occurring polymeric materials. In various embodiments, balloon 210 may not be fully compliant, but is more compliant than template 220 and sufficiently flexible to inflate to a diameter larger than the restraining template 220 diameter at a given pressure, and thereby produces protrusions 212 (as described below). Thus, a semi-compliant or non-compliant balloon can be used. In various embodiments, balloon 210 can be conditioned. Conditioning can comprise stretching, pre-inflating, blow molding, heating, or other process to render the balloon 210 more amenable to use.

In various embodiments, balloon assembly 200 can comprise balloon 210, template 220, and a size limiting layer 215. Similarly, balloon 210 can comprise a composite material, wherein a layer of the composite is size limiting layer 215 and/or template 220. Size limiting layer 215 can be disposed about balloon 210, either between balloon 210 and template 220 or around template 220. Similar to template 220, size limiting layer 215 is configured to control the degree of distension of a compliant balloon 210 during inflation. However, size limiting layer 215 is configured to permit a degree of distension which is greater than the degree that template 220 is configured to permit. In this regard, size limiting layer 215 can possess sufficient flexibility and an upper distension limit which is larger in diameter than the restraining template 220 diameter at a given pressure, allowing size limiting layer 215 to distend about or protrude through aperture 221. In addition, size limiting layer 215 can be configured to have a substantially smooth or wrinkle free surface at the first inflated state. Stated differently, size liming layer is at least slightly strained at the first inflated state.

Size limiting layer 215 can be a sheath, sleeve, layer or other component otherwise configured to at least partially enclose all or a portion of balloon 210. Size limiting layer 215 can act to constrain balloon 210 in a substantially uniform manner once balloon 210 distends to a certain diameter or dimension. Size limiting layer 215 can be configured to operate at pressures of up to 2 atm, up to 5 atm, up to 10 atm, up to 15 atm, up to 20 atm, up to 30 atm, up to 35 atm, up to 45 atm, up to 55 atm, up to 60 atm, or up to any value between about 2 atm and about 60 atm.

In various embodiments, size limiting layer 215 can comprise any flexible, preferably thin material which is inelastic in at least one orientation or has a suitable upper deformation limit in at least one orientation. To withstand higher inflation pressures, size limiting layer 215 can be made of a high strength material. Size limiting layer 215 can be constructed using any material described herein for constructing template 220. Size limiting layer 215 can be an extruded or molded tubular form which is at some point inelastic in a circumferential direction. Alternatively, size limiting layer 215 can comprise a tape wrapped form wherein the tape is, at some point, inelastic or has an upper distension limit in the tapes lengthwise direction.

To form tape-wrapped size limiting layer 215, with reference to FIG. 4A to 4D, a thin film can be slit into relatively narrow widths to form a tape. The tape is helically wrapped onto the surface of a mandrel 12 in two opposing directions 20 and 22, thereby forming a tube of at least two layers 14 and 16. Both layers 14 and 16 can be wrapped with the same pitch angle measured with respect to the longitudinal axis 18 but measured in opposite directions. If, for example, the film layers 14 and 16 are applied at pitch angles of 70° measured from opposite directions with respect to the mandrel's longitudinal axis 18, then included angle A between both 70° pitch angles is 40°.

More than two layers of helically wrapped film may be applied. Alternate layers of film can be wrapped from opposing directions and an even number of film layers can be used whereby an equal number of layers are applied in each direction.

Suitable adhesives may be used to join film wraps together. Such adhesives include fluorinated ethylene propylene (FEP). Alternatively, following completion of film wrapping, the helically wrapped mandrel 12 can be thermally treated at suitable time and temperature to cause adjacent layers 14 and 16 to heat-bond together. Regardless of bonding methodology, the size limiting layer 415 is removed from mandrel 12 and can be placed over the balloon, tensioned longitudinally as needed and affixed in place over the balloon.

During inflation of balloon, size limiting layer 415 can undergo an increase in diameter which results in included angle A being substantially reduced as shown by FIG. 4D. Size limiting layer 415 thus reaches its pre-determined upper distension limit as included angle A approaches zero. This pre-determined limit is greater than the distension limit of template in order to yield a balloon having a varied topography at a second inflated state but one which does not appreciably distend beyond the second inflated state.

Again with reference to FIGS. 2A and 2B(1) to 2B(4), size limiting layer 215 can optionally be adhered to or laminated with balloon 210. If adhered, balloon 210 can aid in recompaction of size limiting layer 215 upon deflation of balloon assembly 200, in particular if balloon 210 is made of an elastomeric materiel. Alternatively, a layer of elastomer, applied to a surface of size limiting layer 215 will cause the size limiting layer 215 to retract substantially to its pre-inflation size as shown by FIG. 4C following deflation.

The film utilized to construct size limiting layer 215 as described above can comprise any flexible, preferably thin material that is substantially inelastic or has an upper distension limit in at least one orientation and has sufficient strength to yield a balloon 210 that can operate at pressures of up to 2 atm, up to 5 atm, up to 10 atm, up to 15 atm, up to 20 atm, up to 30 atm, up to 35 atm, up to 45 atm, up to 55 atm, or up to 60 atm. For example, a film can comprise ePTFE. Other suitable film materials can include other fluoropolymers or non-compliant polymers.

Figure 5A:
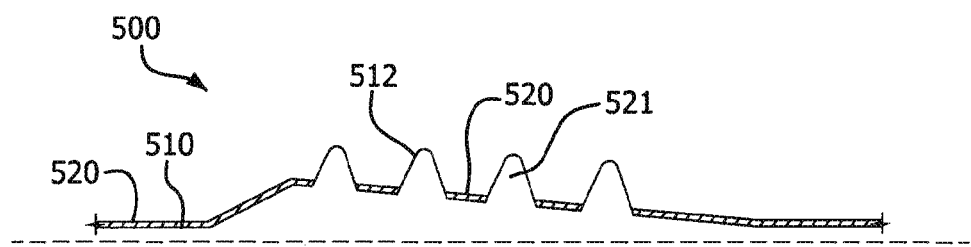
FIG. 5A schematically illustrates a balloon assembly embodiment comprising a tapered balloon and/or size limiting layer.

In various embodiments, size limiting layer 215 can be constructed or conditioned to constrain balloon 210 upon inflation to a generally cylindrical inflation profile. Optionally, with momentary reference to FIG. 5A, size limiting layer 515 can be configured to alter the general profile of balloon 510, e.g., constrain to create a tapered profile, elliptical profile, or a dumbbell profile. In addition, in the event of a failure of balloon 210 (e.g., a rupture), size limiting layer 215 can act to prevent release of undesired debris from the disrupted balloon assembly 200.

In other embodiments, size limiting layer 215 and balloon 210 are combined into a single component. Stated differently, balloon 210 can comprise a compliant, size limiting material. In such embodiments, balloon 210 behaves like a compliant or semi-compliant balloon up to a desired diameter. Once the desired diameter is reached, balloon 210 behaves like a non-compliant balloon, allowing the pressure to increase without resulting in an appreciable increase in a balloon dimension.

In various embodiments, template 220 comprises any size-limited form that acts to constrain balloon 210 along the points of contact. Alternatively, template 220 can comprise a form less compliant than balloon 210 and/or size limiting layer 215 so that balloon 210 is constrained along the points of contact. As such, template 220 is constructed of any material that cannot be appreciably deformed beyond a first inflated state during inflation of balloon 210. Template 220 can be configured as a sleeve, layer, or sheath positioned over balloon 210. For example, template 220 can comprise a generally cylindrical, ellipsoidal, spherical, or similar form that is disposed substantially coaxial to balloon 210. Alternatively, template 220 can be an inner layer that constrains a portion of balloon 210 by being adhered to balloon 200 at selected portions not comprising an aperture 221.

Figure 5B:
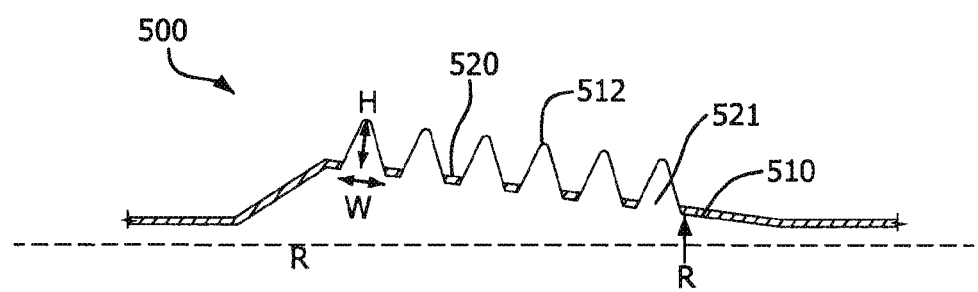
FIG. 5B schematically illustrates a balloon assembly embodiment comprising a tapered template.

In addition, while aperture 221 of template 220 can be spatially configured to create a varied topography, the constraining portion of template 220 can also impact the general profile of balloon 210. For example, as illustrated in FIG. 5B, template 520, at a first inflated state, can have a diameter that is larger or smaller at different locations along the balloon 510, for instance to form a taper. Thus, while balloon 510 can inflate in the shape of a cylinder, template 520 can have a non-cylindrical shape, and this non-cylindrical shape can be the general profile of balloon assembly 500. Such a generally tapered profile can be used to better conform to cardiovascular vessel diameters which change over length, for example. In addition, the lesion or thrombus "scraping" effect of the assembly 500 can be intensified proximally to distally or visa versa due to the varying profile dimensions.

Returning to FIGS. 2A and 2B(1) to 2B(4), template 220 does not substantially deform beyond a first inflated state or deforms to a lesser extent than balloon 210 and size limiting layer 215 in response to inflation of balloon 210. As depicted in FIGS. 2B(3) and 2B(4), balloon 210 and size limiting layer 215 distends beyond template 220 about aperture 221 creating a protrusion 212 at a second inflated state. As shown, at the second inflated state, inflated balloon assembly 200 can have a varied topography in that the surface of balloon assembly 200 has a plurality of peaks and valleys.

In various embodiments, template 220 can comprise a size-limited material or configuration. For example, template 220 can be substantially inelastic in at least one direction or orientation, preferable a direction transverse to the longitudinal axis of balloon assembly 200 and, in various embodiments, template 220 can also comprise a material that has high tensile strength in at least one direction. In an alternate embodiment, the template can comprise a material that has a high strength in both directions so as to prevent the perimeters of apertures 221 from deforming upon expansion of balloon 210. In various embodiments, template 220 can comprise a material that is less compliant than balloon 210 and/or template; thus, at a given pressure, balloon 210 will have a greater degree of distension than template 220.

In an embodiment, template 220 can comprise a high strength, yet flexible material such as ePTFE. High strength provides resistance to deformation in at least one direction such that template 220 can resist expansion of underlying balloon portions beyond the application of a particular force caused by balloon inflation pressures.

In various embodiments, template 220 can be made from a thin, high strength film or tape to forming a template. For example, template 220 can be constructed from a type of ePTFE as described in U.S. Pat. No. 7,306,729, issued Dec. 11, 2007 and entitled, "Porous PTFE Materials And Articles Produced Therefrom," whose contents are herein incorporated by reference. In various embodiments, two to sixty layers of ePTFE as described in U.S. Pat. No. 7,306,729 can comprise template 220. Layers can be circumferentially (i.e., wrapped at about 90° to the longitudinal axis) or helically wrapped (as described previously). In various embodiments, template 220 can be manufactured in a continuous process and then cut to the desired length before being disposed on balloons. Optionally, template 220 can be adhered or laminated to balloon 210 and/or size limiting layer 215.

Template 220 can comprise other materials, such as other fluoropolymers, including polytetrafluoroethylenes with different microstructures from that described in U.S. Pat. No. 7,306,729, so long as they provide sufficient strength and relative lack of compliancy, to produce the desired balloon topography and operate at the previously described pressure thresholds.

In various embodiments, template 220 can also be size-limited but compliant. In such embodiments, template 220 can be formed in a similar manner as size-limited layer and compliant balloon 210. However, in order to create a varied topography, the upper distension limit of template 220 must be less than the upper distension limit of the balloon 210 or the degree of compliancy is less than that for balloon 210.

Template 220 can comprise at least one aperture 221 and, in various embodiments, template 220 can comprise an aperture pattern and/or a plurality of apertures. Apertures 221 can be present in template 220 prior to inflation or be formed or increase in size upon inflation.

Aperture 221 can comprise an opening or weakened site in the template material. In this regard, an opening can be a hole, cut, or any other discontinuous section of the template material. For example, a hole could be formed by puncturing template 220. Alternatively, aperture 221 can comprise an area of template 220 where a portion of the material has been removed or otherwise weakened such that the weakened portion at least partially deforms or detaches in response to inflation of balloon 210 and permits distension beyond the first inflated state. Apertures 221 can be formed by any suitable means, including cutting, stamping, laser cutting, perforating, and/or punching/puncturing and/or the like. In various embodiments, template 220 can comprise a net like structure.

Optionally, template can comprise apertures that vary in size. Increasing the size the apertures can allow for a wider (or "coarser") protrusion. By combining varying aperture sizes with a tapered template profile, as shown in FIG. 5B, the "scraping" effect of the assembly can be intensified proximally to distally or visa versa due to the different protrusion heights.

With reference again to FIGS. 2A and 2B(1) to 2B(4), template 220 can be configured such that apertures 221 are formed or increase in size upon inflation. For example, a template 220 comprising a tape wrapped, woven, or braided membrane around balloon 210 can be constructed, e.g. wrapped, woven, or braided, such that apertures 221 are formed by leaving a space between tape edges and/or apertures 221 form or increase in size between tape edges upon inflation of balloon 210. In an embodiment, the angle of the tape material can change relative to the longitudinal axis of the balloon upon inflation and/or the tape material can narrow in width as the balloon assembly is expanded, thus creating apertures 221.

Figure 6A:
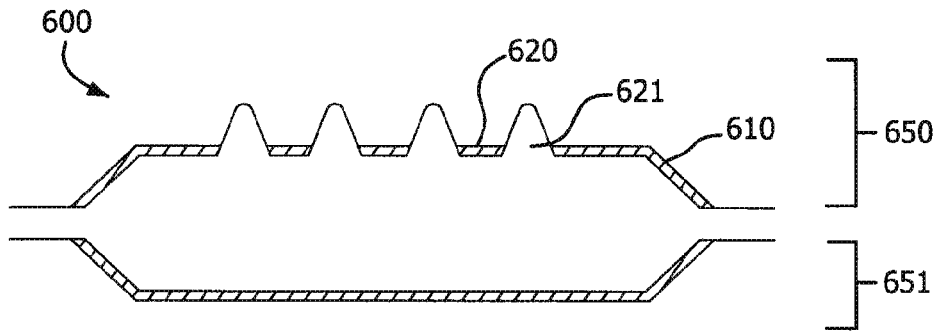
FIGS. 6A and 6B illustrate a cross-sectional view of a varied topography balloon assembly embodiment wherein a plurality of apertures are located on a first section of the template and no apertures are located on a second section of template.
Figure 6B:
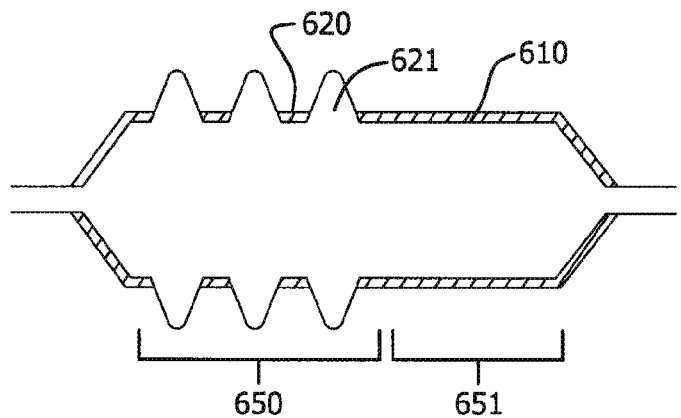

In addition, the varied topography can vary longitudinally along the length of the balloon and/or can vary circumferentially about the perimeter of the balloon. For example, with reference to FIG. 6(A-B), balloon assembly 600 can comprise a template 620 having a first pattern of apertures 621 on first section 650 of balloon 610 and a second pattern of aperture or zero apertures on a second section 651. Similarly, the longitudinal and/or circumferential variation can be random or follow a pre-defined pattern. Such balloon assemblies can be used for performing interventional procedures in combination. For example, such a balloon configured with zero apertures on one half the length of the balloon assembly and apertures on the remainder of the assembly can be used to perform both thrombectomy (with the apertured portion of the assembly) then Percutaneous Transluminal Angioplasty (PTA) (with the non-apertured portion), all without the exchange of devices.

The balloon assembly can be selectively alternated between the various inflated states, e.g., between a first inflated state and a second inflations state. A specific inflated state can be determined by measuring the volume injected into balloon assembly and/or pressure levels within balloon assembly. By selectively introducing or withdrawing a fluid by a predetermined amount, balloon assembly can transition from one inflated state to another. In an embodiment, the balloon assembly can be configured to pulsate between the various inflations states.

In various embodiments, balloon assembly can optionally comprise a protective cover. A protective cover can be a sleeve or sheath that covers at least a portion of template. The protective cover can be delivered with the balloon assembly into the body and be retracted to expose balloon assembly 200 while within the body.

With the described components, one can adapt the compliance of the balloon, a template, an aperture pattern, inflation pressures and extensibility of a size limiting layer to control the topography of a balloon assembly. For example, an aperture pattern can comprise many small apertures to obtain a "fine texture" pattern or can comprise fewer larger openings to obtain a more "coarse texture" pattern. As one can appreciate, any possible aperture pattern, or combinations of aperture patterns, is contemplated herein. For example, a first portion of a template can comprise a square grid like aperture pattern and a second portion of a template can comprise a diamond shaped pattern.

In other embodiments, a balloon expanding through a template can define ridges and troughs which, for example, run parallel to the longitudinal axis of the balloon. In one embodiment, these provide for blood perfusion between balloon and vessel wall during a treatment when the balloon is expanded.

In other embodiments, protrusions 212 can form at a first inflated state as depicted in FIG. 2C, and then upon inflation to a second inflated state, having a pressure greater than the first, template 220 can distend and the surface of balloon 210 is smooth, as depicted in FIG. 2B. In an embodiment, template 220 can be partially or selectively distensible. For example, a 4 mm template that is distensible up to 8 mm can overlay a balloon and/or a size limiting layer. Balloon 210 is inflated to 2 atm and the template acquires its first distension profile so that protrusions form. Upon further inflation up to 4 atm, the template can distend to its second distension profile or its maximum size. The maximum size of template 220 can correspond to the maximum size of balloon 210 and/or size limiting layer 215. In other embodiments, template 220 can be frangible and made to break or stretch at a selected inflation pressure to then reduce the height, at least partially, of some or all of protrusions 212 to allow for increased contact between the balloon surface and the target tissue(s) at a higher pressure. Such embodiments can be used to perform both thrombectomy (at the first inflated state) then Percutaneous Transluminal Angioplasty (PTA) (at the second inflated state), all without the exchange of devices.

Figure 7A:
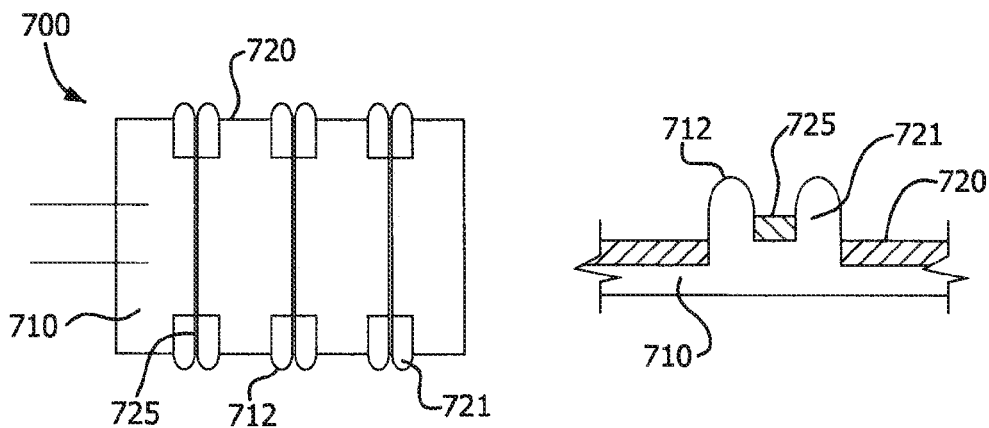
FIG. 7 A schematically illustrates a varied topography balloon assembly embodiment of the present disclosure comprising two templates.
FIG. 7B illustrates a close up, cross-sectional view about an aperture of a varied topography balloon assembly embodiment illustrated in FIG. 7A.
Figure 7B:
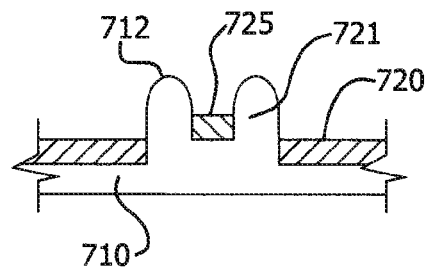

In various additional embodiments, multiple templates can be used with one compliant balloon to further control and further vary topography. With reference to FIGS. 7A and 7B, balloon assembly 700 comprises balloon 710 and at least two templates 720 and 725. Template 720 can be disposed coaxially or substantially coaxially over balloon 710, and secondary template 725 can be disposed coaxially or substantially coaxially over template 720. Upon inflation of balloon 710 to the second inflated state, as depicted in FIG. 7A, both template 720 and secondary template 725 act to constrain balloon 710 and have aperture patterns to allow balloon 710 to expand through apertures 721 in each template. In an embodiment, template 720 and secondary template 725 can act to shape the topography of inflated balloon assembly 700. Template 720 can create a "coarse" varied topography, and secondary template 725 is selectively positioned to constrain a portion of protrusion 712 and create a "fine" aperture pattern. Protrusion 712 is thus further constrained by secondary template 725 to form at least two protrusions or protrusions of different size or shape and create a finer or varied aperture pattern.

Optionally, each template can have different upper distension limits such that the varied topography can vary by varying the distension of balloon 710. In such embodiments, balloon assembly 700 can have three or more inflated states. It is contemplated that any number of templates can be layered in a balloon assembly to vary and refine topography. In addition, balloon assembly 700 can optionally comprise a size limiting layer as described herein.

Figure 9:
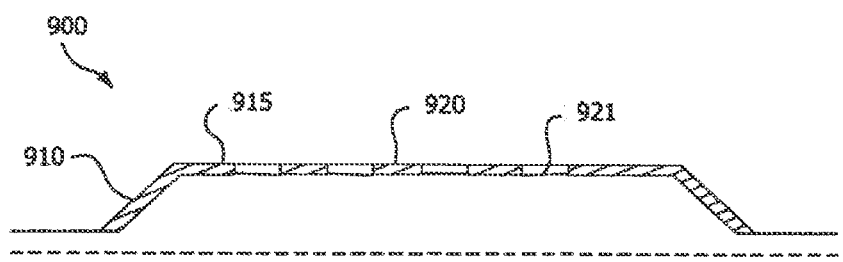
FIG. 9 illustrates a varied topography balloon assembly embodiment wherein the balloon comprises a wall with regions of reduced compliance than other more distensible regions.
Figure 18:
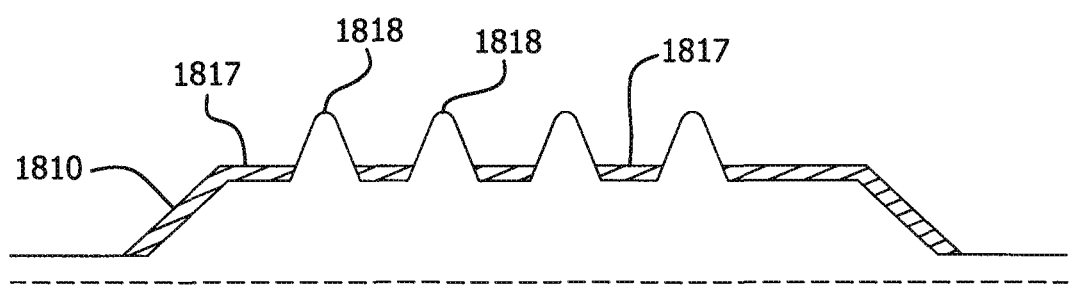
FIG. 18 illustrates a balloon assembly embodiment wherein the balloon and size limiting layer is perfusable.

FIG. 9 and FIG. 18 illustrate a varied topography balloon assembly embodiment wherein the balloon comprises a wall with regions of reduced compliance than other more distensible regions;

With reference to FIG. 18, balloon 1810 can comprise a wall having portions 1817 of reduced or less compliance than other, more distensible portions 1818 of wall. The other portions 1818 being essentially the "apertures" that expand outwardly relative to the portions of reduced or less compliance. The more distensible portions 1818 can comprise an upper distension limit. The portions 1817 of reduced compliance can be formed through laser densification or by imbibing with a polymer that reduces the compliance in the imbibed region. In an embodiment, the regions 1817 of reduced compliance have substantially the same thickness as the more distensible regions 1818. Similar, with other embodiments described herein, balloon 1810 can be formed via tape wrapping or extrusion, and can comprise ePTFE or any other material wherein the compliancy can be varied at discrete sites.

Similarly, in an embodiment, the balloon can comprise a plurality of protrusions in the form of knob-like features. Unlike the previously described embodiment, the distensiblity of the sites need not vary along the balloon material. Here, the protrusion is pre-formed into the balloon. To form a knob-like feature on the balloon, a balloon form can be placed onto a mandrel or constructed on a mandrel which has an aperture or recessed site thereon corresponding to the site of a knob-like feature. In an embodiment, a heated element can be used to push the knob-like feature into the aperture or recess and set the feature into the balloon wall. Similarly, a lower melt thermoplastic material can be imbibed into the balloon wall at the site of the recess and aperture with the application of pressure and heat, and allowed to cure while pressure is still applied and the wall is recessed. In another embodiment, a vacuum can be applied to the apertures (or pressure applied to the balloon) such that a recessed site is formed on the balloon surface. The balloon can then be cured while in this configuration.

Figure 19A:
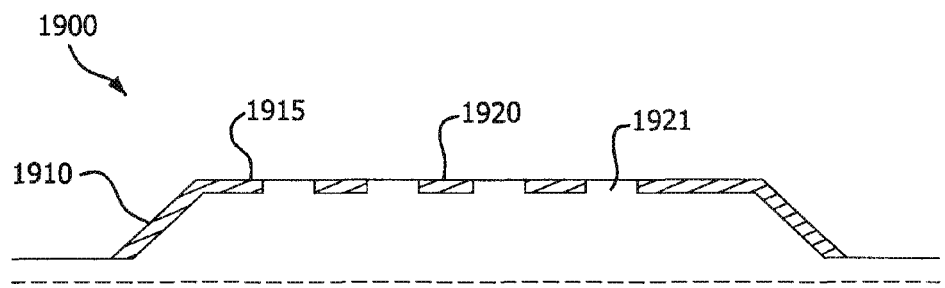
FIGS. 19A-B illustrates a varied topography balloon assembly embodiment wherein the balloon comprises a wall with regions of reduced compliance than other more distensible regions.
Figure 19B:
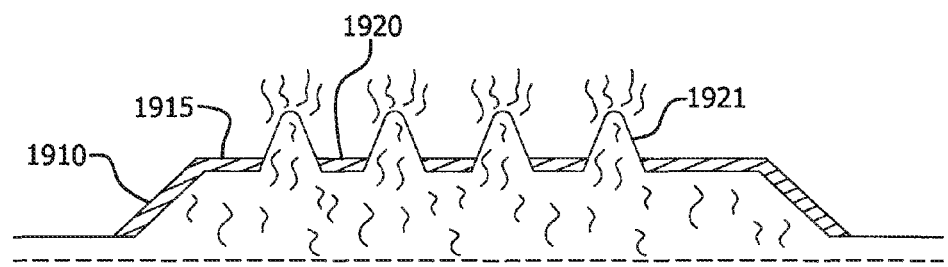

In further embodiments, with reference to FIG. 19, balloon assemblies 1900 as described herein can be perfusable. For example, balloon 1910, size limiting layer 1915, and optionally, template 1920 can comprise a porous material. In addition, balloon 1910, size limiting layer 1915, and optionally, template 1920 can comprise a variably perfusable material. In various embodiments, prior to protrusion, the porosity of the material or the internal pressure is low enough to not perfuse or minimally perfuse. For example, upon expansion of balloon 1910 and its protrusion through apertures 1921, localized forces can cause the microstructure of the material protruding through apertures 1921 to become more porous, allowing the therapeutic agent to be released from balloon 1910. In other embodiments, the porosity of the microstructure is not altered but rather the water entry pressure of the balloon material is such that the balloon does not perfuse until a certain threshold pressure. As such, balloon 1919 can be configured not to perfuse until the second inflated state is obtained. In addition, balloon 1910 can be configured to perfuse along only a portion, e.g., the regions of balloon 1910 that upon inflation, protrude through apertures 1921.

In various embodiments, a balloon assembly can further comprise a therapeutic agent disposed on, inside of, temporarily filling, or otherwise be integrated with the template. Similarly, a balloon assembly can comprise a therapeutic agent disposed on an inner or outer surface of the balloon or template, or inside balloon. In an embodiment, a therapeutic agent can be coated on a portion of the elongate member underlying the balloon. Therapeutic agent formula can comprise a liquid or solid form. Liquid from can be of a desired viscosity suitable for the treatment desired.

Figure 8:
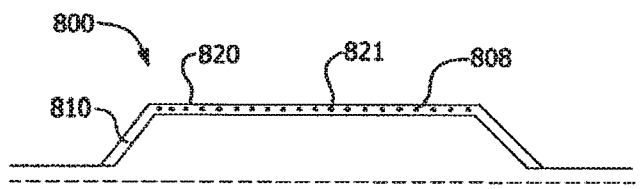
FIG. 8 illustrates a varied topography balloon assembly comprising a therapeutic agent, in accordance with various embodiments.

With reference to FIG. 8, balloon assembly 800 comprises balloon 810 disposed within template 820, and therapeutic agent 808 is disposed between balloon 810 and template 820. Upon inflation of balloon 810, therapeutic agent 808 can be conveyed through an aperture 821 of template 820 and be released at a localized portion of the body. In an embodiment, aperture 821 can form upon inflation thus containing therapeutic agent 808 until balloon assembly 800 is inflated.

Similarly, therapeutic agent can be disposed within aperture. Upon inflation of balloon, therapeutic agent can be conveyed beyond aperture by protrusion and be directed to a surrounding tissue and/or a localized portion of the body. In various embodiments, the therapeutic agent formula can be in a solid or viscous form to maintain location within aperture. Alternatively, therapeutic agent, positioned within aperture can be protected by a sheath until placed at a treatment site whereupon the sheath can be retracted.

In addition, aperture can be configured to limit the release of therapeutic agent until inflation is underway. For example, apertures can comprise a conical or other tapered shape, wherein the aperture defines a smaller area on the outer face than on the inner face. Aperture can be configured to enlarge upon inflation to facilitate release of therapeutic agent. In addition, balloon assembly can comprise a releasable cover to limit or prevent the release of therapeutic agent.

Any therapeutic agent that aids in any procedure, e.g., diagnostic or therapeutic procedures, or that aids in providing a therapeutic and/or curative effect is contemplated and suitable for use with balloon assemblies disclosed herein. In particular, therapeutic agents that become safer, effective, or achieve another benefit from localized delivery are useful with balloons disclosed herein. Among others, suitable therapeutic agents include anti-proliferative, anti-inflammatory, fibrolytic, thrombolytic, anti-phlogistic, anti-hyperplastic, anti-neoplastic, anti-mitotic, cytostatic, cytotoxic, anti-angiogenic, anti-restenotic, microtubule inhibiting, anti-migration or anti-thrombotic therapeutic agents.

For example, suitable therapeutic agents can include: abciximab, acemetacin, acetylvismione B, aclarubicin, ademetionine, adriamycin, aescin, afromoson, akagerine, aldesleukin, amidorone, aminoglutethemide, amsacrine, anakinra, anastrozole, anemonin, anopterine, antimycotics, antithrombotics, thrombolytics such as tissue plasminogen activator (tPA), apocymarin, argatroban, aristolactam-AII, aristolochic acid, arsenic and arsenic-containing oxides, salts, chelates and organic compounds, ascomycin, asparaginase, aspirin, atorvastatin, auranofin, azathioprine, azithromycin, baccatine, bafilomycin, basiliximab, bendamustine, benzocaine, berberine, betulin, betulinic acid, bilobol, biolimus, bisparthenolidine, bleomycin, bombrestatin, boswellic acids and their derivatives, bruceanoles A, B and C, bryophyllin A, busulfan, antithrombin, bivalirudin, cadherins, camptothecin, capecitabine, o-carbamoylphenoxyacetic acid, carboplatin, carmustine, celecoxib, cepharanthin, cerivastatin, CETP inhibitors, chlorambucil, chloroquine phosphate, cictoxin, ciprofloxacin, cisplatin, cladribine, clarithromycin, colchicine, concanamycin, coumadin, C-Type natriuretic peptide (CNP), cudxaisoflavone A, curcumin, cyclophosphamide, cyclosporine A, cytarabine, dacarbazine, daclizumab, dactinomycin, dapson, daunorubicin, diclofenac, 1,11-dimethoxycanthin-6-one, docetaxel, doxorubicin, dunaimycin, epirubicin, epothilone A and B, erythromycine, estramustine, etoposide, everolimus, filgrastim, fluroblastin, fluvastatin, fludarabine, fludarabin-5'-dihydrogenphosphate, fluorouracil, folimycin, fosfestrol, gemcitabine, ghalakinoside, ginkgol, ginkgolic acid, glycoside 1 a, 4-hydroxyoxycyclophosphamide, idarubicin, ifosfamide, josamycin, lapachol, lomustine, lovastatin, melphalan, midecamycin, mitoxantrone, nimustine, pitavastatin, pravastatin, procarbazin, mitomycin, methotrexate, mercaptopurine, thioguanine, oxaliplatin, bismuth and bismuth compounds or chelates, irinotecan, topotecan, hydroxycarbamide, miltefosine, pentostatine, pegaspargase, exemestane, letrozole, formestane, SMC proliferation inhibitor-2co, mitoxantrone, mycophenolate mofetil, c-myc antisense, b-myc antisense, [3-1apachone, podophyllotoxin, podophyllic acid-2-ethylhydrazide, molgramostim (rhuGM-CSF), peginterferon ct-2b, lanograstim (r-HuG-CSF), macrogol, selectin (cytokin antagonist), cytokin inhibitors, COX-2 inhibitor, NFkB, angiopeptin, monoclonal antibodies which inhibit muscle cell proliferation, bFGF antagonists, probucol, prostaglandins, 1-hydloxyl 1-methoxycanthin-6-one, scopolectin, NO donors, pentaerythiltol tetranitrate, syndxloimines, S-nitrosodeilvatives, tamoxifen, staurosporine, [3-oestradiol, ct-oestradiol, oestriol, oestrone, ethinyloestradiol, medroxyprogesterone, oestradiol cypionates, oestradiol benzoates, tranilast, kamebakaurin and other terpenoids, which are used in the treatment of cancer, verapamil, tyrosine kinase inhibitors (tyrphostins), paclitaxel, paclitaxel derivatives, 6-c-hydroxy paclitaxel, 2'-succinylpaclitaxel, 2'-succinylpaclitaxeltilethanolamine, 2'-glutarylpaclitaxel, 2'-glutarylpaclitaxeltilethanolamine, T-O-ester of paclitaxel with N-(dimethylaminoethyl) glutamide, T-O-ester of paclitaxel with N-(dimethylaminoethyl)glutamidhydrochloride, taxotere, carbon suboxides (MCS), macrocyclic oligomers of carbon suboxide, mofebutazone, lonazolac, lidocaine, ketoprofen, mefenamic acid, piroxicam, meloxicam, penicillamine, hydroxychloroquine, sodium aurothiomalate, oxaceprol, [3-sitosteiln, myrtecaine, polidocanol, nonivamide, levomenthol, ellipticine, D-24851 (Calbiochem), colcemid, cytochalasinA-E, indanocine, nocadazole, S 100 protein, bacitracin, vitronectin receptor antagonists, azelastine, guanidyl cyclase stimulator tissue inhibitor of metal proteinasel and 2, free nucleic acids, nucleic acids incorporated into virus transmitters, DNA and RNA fragments, plasminogen activator inhibitor-1, plasminogen activator inhibitor-2, antisense oligonucleotides, VEGF inhibitors, IGF-1, active substances from the group of antibiotics such as cefadroxil, cefazolin, cefaclor, cefotixin, tobramycin, gentamycin, penicillins such as dicloxacillin, oxacillin, sulfonamides, metronidazole, enoxoparin, desulphated and N-reacetylated hepailn, tissue plasminogen activator, GpIIb/IIIa platelet membrane receptor, factor Xa inhibitor antibodies, hepailn, hirudin, r-hirudin, PPACK, protamine, prourokinase, streptokinase, warfarin, urokinase, vasodilators such as dipyramidol, trapidil, nitroprussides, PDGF antagonists such as triazolopyilmidine and seramine, ACE inhibitors such as captopril, cilazapill, lisiropill, enalapril, losartan, thioprotease inhibitors, prostacyclin, vapiprost, interferon a, [3 and y, histamine antagonists, serotonin blockers, apoptosis inhibitors, apoptosis regulators such as p65, NF-kB or Bcl-xL antisense oligonucleotides, halofuginone, nifedipine, tocopherol tranilast, molsidomine, tea polyphenols, epicatechin gallate, epigallocatechin gallate, leflunomide, etanercept, sulfasalazine, etoposide, dicloxacillin, tetracycline, triamcinolone, mutamycin, procainimide, retinoic acid, quinidine, disopyramide, flecainide, propafenone, sotolol, naturally and synthetically obtained steroids such as inotodiol, maquiroside A, ghalakinoside, mansonine, strebloside, hydlocortisone, betamethasone, dexamethasone, non-steroidal substances (NSAIDS) such as fenoporfen, ibuprofen, indomethacin, naproxen, phenylbutazone and other antiviral agents such as acyclovir, ganciclovir and zidovudin, clotilmazole, flucytosine, griseofulvin, ketoconazole, miconazole, nystatin, terbinafine, antiprozoal agents such as chloroquine, mefloquine, quinine, furthermore natural terpenoids such as hippocaesculin, barringtogenol C21-angelate, 14-dehydloagrostistachin, agroskeiln, agrostistachin, 17-hydroxyagrostistachin, ovatodiolids, 4,7-oxycycloanisomelic acid, baccharinoids B1, B2, B3 and B7, tubeimoside, bruceantinoside C, yadanziosides N, and P, isodeoxyelephantopin, tomenphantopin A and B, coronailn A, B, C and D, ursolic acid, hyptatic acidA, iso-iildogermanal, cantenfoliol, effusantin A, excisaninA and B, longikauiln B, sculponeatin C, kamebaunin, leukamenin A and B, 13,18-dehydro-6-alpha-senecioyloxychapariln, taxamaiiln A and B, regenilol, triptolide, cymarin, hydroxyanopterin, protoanemonin, chelibu- rin chloride, sinococuline A and B, dihydronitidine, nitidine chloride, 12-beta-hydroxypregnadien-3,20-dion, helenalin, indicine, indicine-N-oxide, lasiocarpine, inotodiol, podophyllotoxin, justicidin A and B, larreatin, malloterin, mallotochromanol, isobutyrylmallotochromanol, maquiroside A, marchantin A, cantansin, lycoridicin, margetine, pancratistatin, liilodenine, bisparthenolidine, oxoushinsunine, periplocoside A, ursolic acid, deoxypsorospermin, psycorubin, ilcin A, sanguinailne, manu wheat acid, methylsorbifolin, sphatheliachromen, stizophyllin, mansonine, strebloside, dihydrousambaraensine, hydroxyusambailne, strychnopentamine, strychnophylline, usambarine, usambarensine, liriodenine, oxoushinsunine, daphnoretin, lariciresinol, methoxylailciresinol, sclerosant agents, syringaresinol, sirolimus (rapamycin), rapamycin combined with arsenic or with compounds of arsenic or with complexes containing arsenic, somatostatin, tacrolimus, roxithromycin, troleandomycin, simvastatin, rosuvastatin, vinblastine, vincilstine, vindesine, thalidomide, teniposide, vinorelbine, trofosfamide, treosulfan, tremozolomide, thlotepa, tretinoin, spiramycin, umbelliferone, desacetylvismioneA, vismioneA and B, zeoiln, fasudil.

Figure 10A:
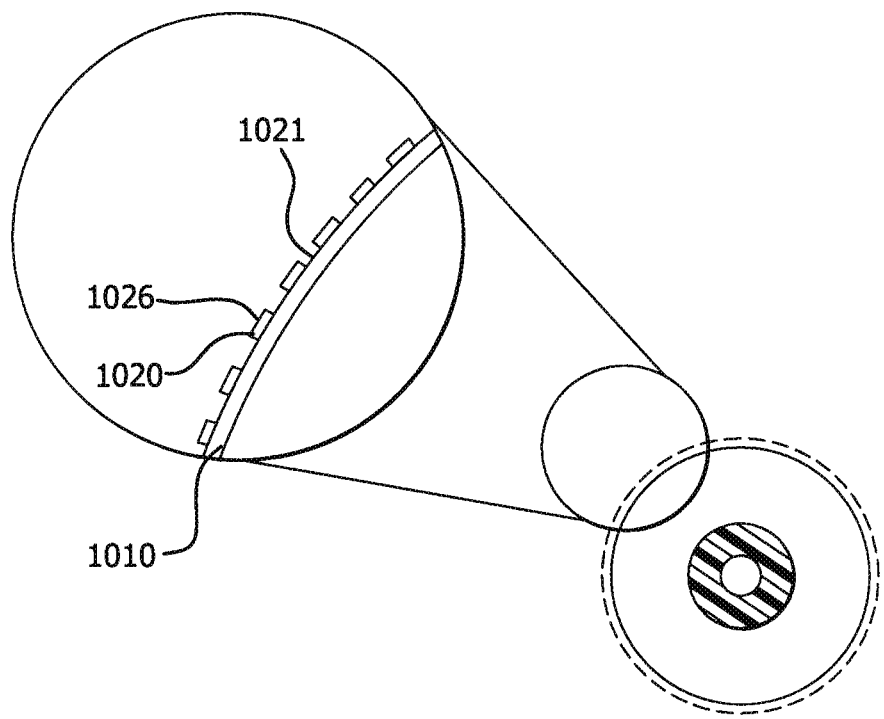
FIG. 10A illustrates a cross-sectional view of a balloon assembly embodiment wherein the overlying template comprise rigid elements.
Figure 10B:
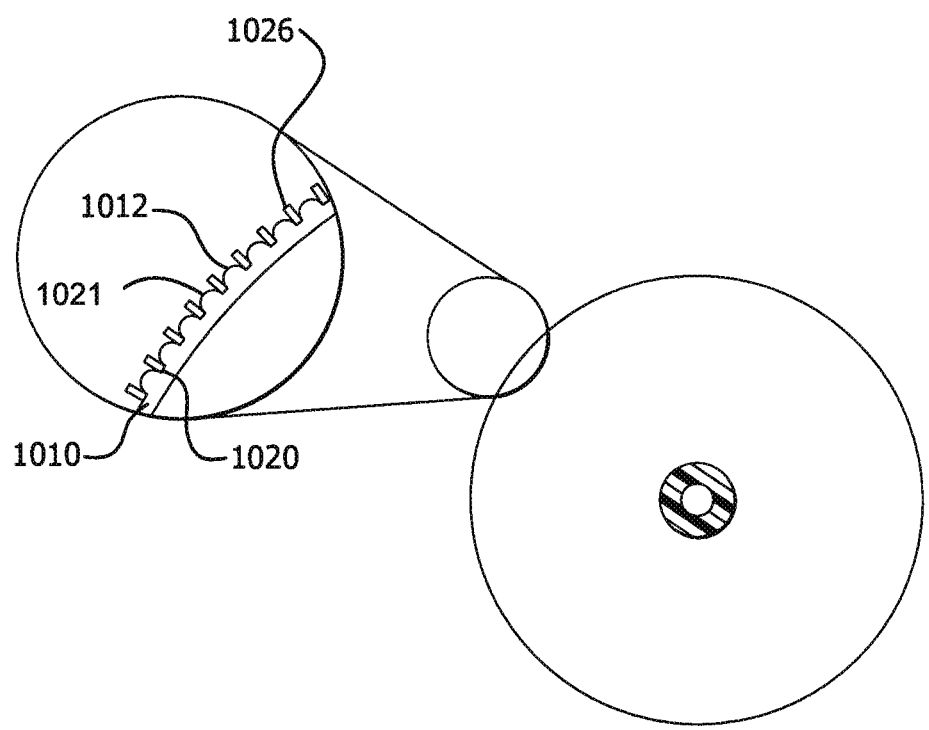
FIG. 10B illustrates a cross-sectional view of a balloon assembly embodiment depicted in FIG. 10A with the rigid elements outwardly rotated.
Figure 10C:
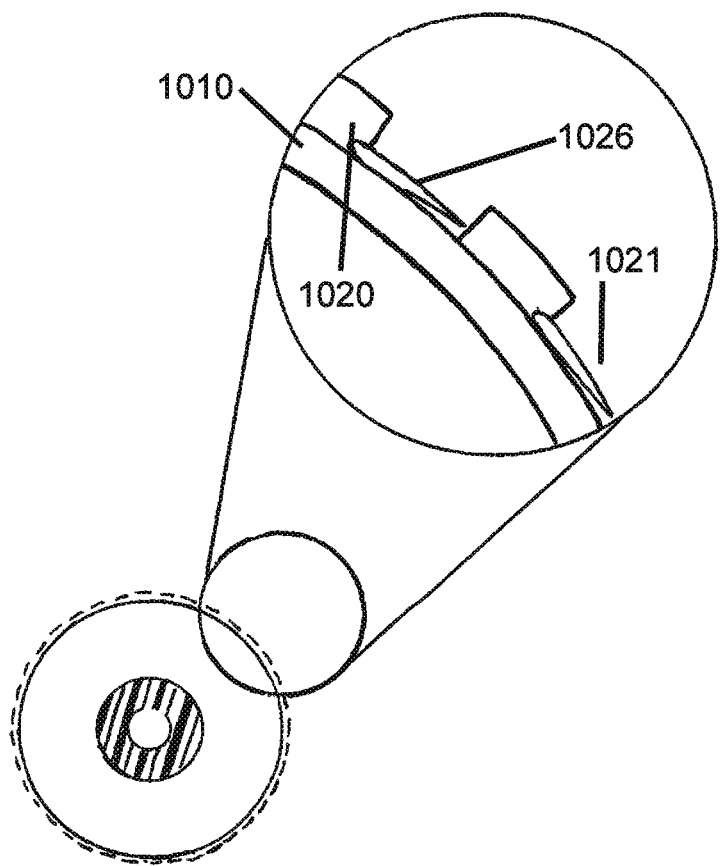
FIG. 10C illustrates a cross-sectional view of a balloon assembly embodiment wherein the overlying template comprises rigid elements having a piercing or sharp tip that is attached to template at its proximal base.
Figure 10D:
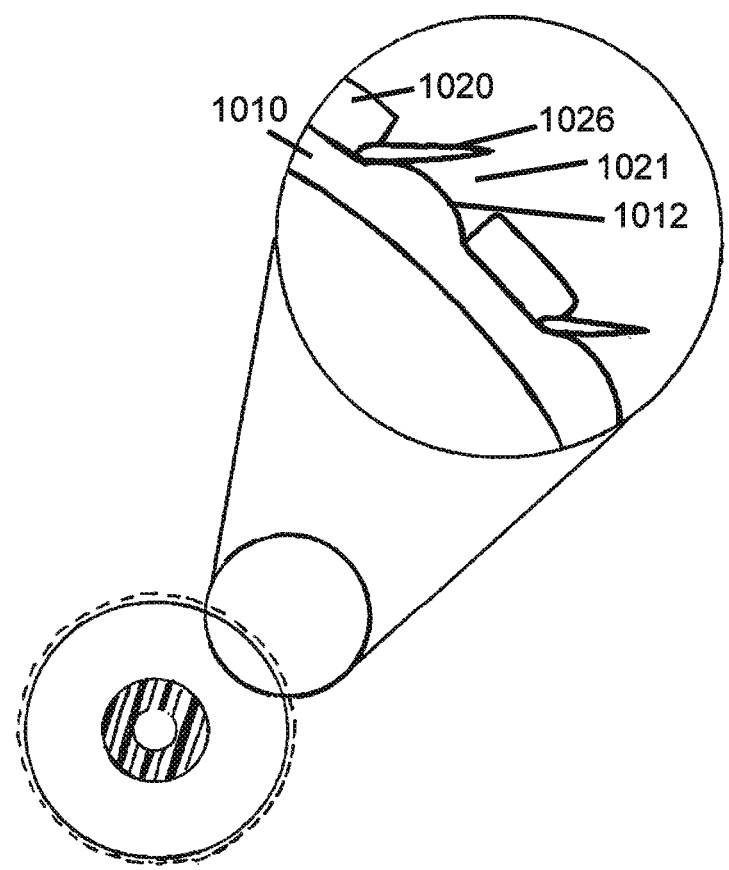
FIG. 10D illustrates a cross-sectional view of a balloon assembly embodiment wherein the overlying template comprises rigid elements of FIG. 10C outwardly rotated.
Figure 10E:
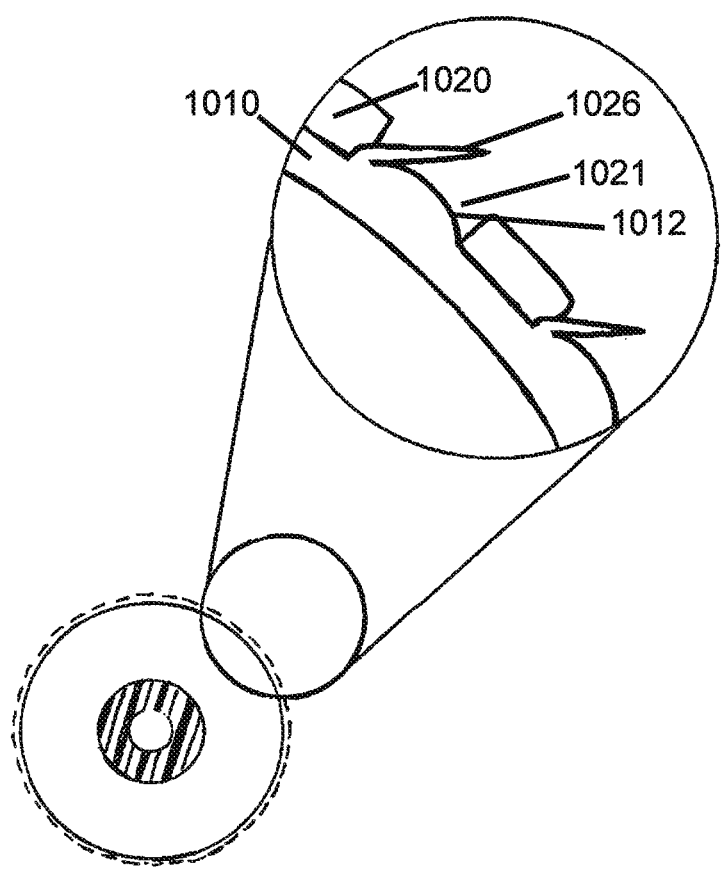
FIG. 10E illustrates a cross-sectional view of a balloon assembly embodiment wherein the overlying template comprises rigid elements having a lumen therethrough which is in fluid communication with the balloon.

In various embodiments, with reference to FIGS. 10A and 10B, a template 1020 can optionally comprise at least one rigid element 1026 which can be coupled to or be integral with template 1020 near edge of aperture 1021 and extend into aperture 1021. Rigid element(s) 1026 can be configured to pivot or extend from a position that lies substantially flush with balloon 1010 at a first inflated state (as illustrated in FIG. 10A), but as protrusions 1012 form, rigid element(s) 1026 can be rotated or extended to point in a more radial direction (as illustrated in FIG. 10B). Rigid elements 1026 can be configured to be rough and/or sharp. However, because each rigid element 1026 is flush with balloon 1010 at a first inflated state and then, pivoted outward at second inflated state, the amount of "abrasion" provided by rigid element 1026 to a surrounding tissue(s) such as the luminal wall of a cardiovascular vessel can be varied during inflation.

Rigid elements 1026 can be constructed by attaching the base of the element 1026 to template 1020 or balloon 1010 at the point underlying template 1020 and passing through template 1020. In some embodiments, rigid element 1026 can comprise a lumen, e.g. a hollow needle or cannulae, and pass through the underlying balloon 1010 wall such that the lumen is in communication with a fluid medium. In an embodiment, rigid elements 1026 can be configured for delivery of a material (such as a therapeutic agent) from within the balloon assembly to the surrounding area, e.g. the vessel walls. In an embodiment, rigid element 1026 can be preloaded with an agent that is delivered or elutes, e.g., stored within a lumen, at least partially coated thereon, or at least partially imbibed therein. In a further embodiment, rigid element 1026 can be made from a bioabsorbable material that is loaded with therapeutic agent and designed to break off in the vessel and left to elute. In another embodiment, a lumen of rigid element 1026 can be in communication with a fluid reservoir that is either the inflation media or located around the balloon and compressed by inflation of balloon 1010 leading to elution of the therapeutic agent through the lumen.

Figure 11:
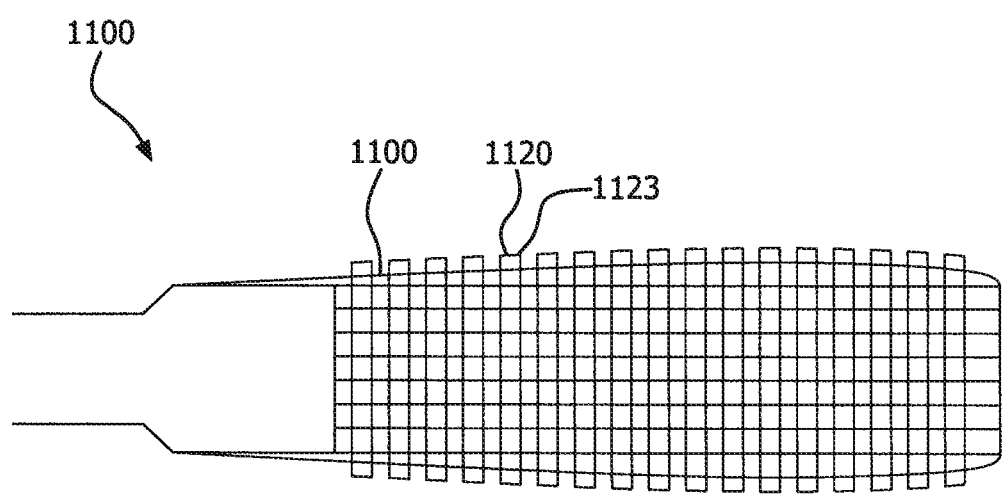
FIG. 11 illustrates a inflated balloon assembly comprising a wire template.

Similarly, in various embodiments, a template can also comprise wires or blades. With momentary reference to FIG. 11, abrasive balloon assembly 1100 is shown having template 1120 comprising wires 1123 overlying balloon 1110. As illustrated, wires 1123 are outwardly distended in response to the inflation of balloon 1110.

In various embodiments, the balloon assembly embodiments described herein can optionally comprise electrical components (e.g., circuitry applied to the balloon surface via methods known in the art). Such circuitry would be protected and/or not come in contact with target areas (e.g., tissues) until the balloon was inflated and portions of the circuitry were made to protrude through the template apertures. Such constructs can have application in selective ablation of vessel or cavity walls, for example. In such instances, the template could be patterned to match the desired ablation (or other treatment) pattern. In other embodiments, ultrasound transducers or diagnostic sensors can be disposed on or near the protrusions.

It should also be noted that templates, depending on their shape, size and general configuration can also be made to provide protection to the underlying balloon, e.g., provide puncture resistance.

Figure 12:
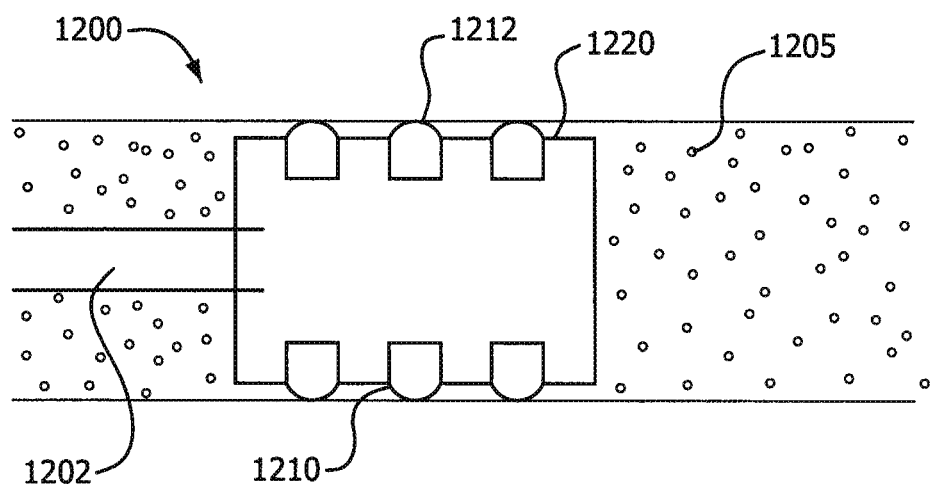
FIG. 12 illustrates a balloon assembly in accordance with various embodiments within the vasculature.

In various embodiments, balloon assemblies disclosed herein can be used in the vasculature. For example, FIG. 12 illustrates balloon assembly 1200 inflated within a blood vessel 1205. Catheter 1202 is shown coupled to balloon 1210. Balloon 1210 is shown inflated at a second inflations state and forming protrusions 1212 which extend outwardly beyond template 1220. Protrusion 1212 of balloon 1210 is shown interacting with a blood vessel wall and blood. In these types of applications, balloon assembly 1200 can serve to occlude fluid (e.g., blood) flow within a lumen or cavity. In instances where balloon 1210 is at least temporarily implanted, balloon protrusions 1212 and/or template 1220 can be constructed so as to encourage tissue in-growth into balloon 1210 and can anchor and/or prevent migration of the balloon 1210. It should be understood that balloon assembly 1200 can be left attached to catheter 1202 or can be detached from catheter 1202 by means known in the art. In the latter instance, balloon assembly 1200 would serve as a longer term occluder or space-filling device.

Figure 17:
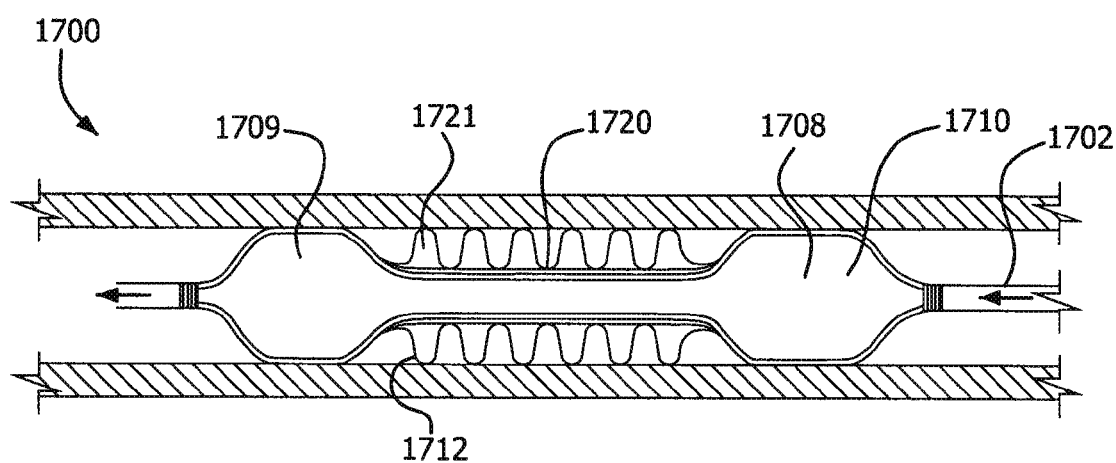
FIG. 17 illustrates a balloon assembly embodiment wherein a template is located on an intermediate section of a balloon.

In one embodiment, with reference to FIG. 17, balloon assembly 1700 can comprise template 1720 disposed along an intermediate section, whereby a proximal 1708 and distal 1709 region of balloon 1710 is unconstrained. Template 1720 comprises apertures 1721 as described previously. Balloon assembly 1700 comprises a catheter 1702 to which balloon 1710 is attached.

Upon inflation, balloon 1710 inflates and expands in size preferentially in the regions located to each side of the intermediate section of balloon 1710 covered and constrained by template 1720. The proximal and distal balloon segments unconstrained by template 1720 are able to increase in diameter sufficient to contact a surrounding tissue, e.g., the luminal wall of a cardiovascular vessel, while the intermediate, constrained section remains at a smaller diameter. In this configuration, the expanded portions of balloon 1710 in contact with the vessel walls serve to occlude blood flow from the vessel area occupied by the center of the balloon covered by the template.

In a further embodiment, the intermediate section of balloon 1710 constrained by template 1720 can be designed to subsequently release a therapeutic agent into the vessel area isolated from blood flow. Balloon 1710 and/or template 1720 is configured to perfuse. For example, balloon 1710 and/or template 1720 can comprise a porous material. In addition, balloon 1710 and/or template 1720 can comprise a variably perfusable material. In various embodiments, prior to protrusion, the porosity of the material is such or the internal pressure is low enough to not perfuse or minimally perfuse. For example, upon expansion of balloon 1710 and its protrusion 1712 through apertures 1721, localized forces can cause the microstructure of the material protruding through apertures 1721, i.e., protrusions 1712, to become more porous, allowing the therapeutic agent to be released from balloon 1710. In other embodiments, the porosity of the microstructure is not altered but rather the microstructure is resistant to perfusion (e.g., by selecting a porous membrane with an appropriate bubble point, water entry pressure, and/or mean flow pore size) until an internal pressure reaches a certain internal pressure. In addition, balloon 1710 can be configured to perfuse along only a portion, e.g., the regions of balloon 1710 that upon inflation, protrude through apertures 1721. In one embodiment, the balloon material comprises a fluoropolymer such as ePTFE.

In various embodiments, perfusing balloons as described herein can be at least partially coated with polyvinyl alcohol (PVA) to render them more hydrophilic. This could result in the lowering of the perfusion pressure at select sites or across the entire surface.

Similarly, in various embodiments, perfusing balloons as described herein can further comprise an outer layer or coating that is oleophobic or render it to have a low surface energy. For example, as described in U.S. Pat. No. 5,586,279 by Wu, which is hereby incorporated by reference, the reaction product of perfluoroalkyl alkyl alcohol compounds with selected diisocyanates can be applied to the outermost membrane, whether it be the weeping control layer, the reinforcing layer, or the sealing layer, in order to lower the surface energy of the microstructure while preserving the microporous structure. Other examples of oleophobic coatings are described in the following, which are hereby incorporated by reference in their entireties: U.S. Pat. No. 5,342,434 to Wu; U.S. Pat. No. 5,460,872 to Wu and Kaler; WO 2006/127946 to Gore Enterprise Holding; and Canadian Patent No. 2609327 to Freese.

In other embodiments, a balloon assembly placed for long term implantation and detached from a catheter can be constructed so as to feature one or more lumens (e.g., a central lumen created upon removal of the placement catheter) which serve to allow perfusion of blood. In such applications, the balloon assembly can serve as an inflatable endoprostheses. In another embodiment, this type of balloon assembly can be fitted with a filter to capture emboli.

In various embodiments, balloon assemblies in accordance with the present disclosure can have pre-configured varied topographies or textured topographies. Stated another way, a particular topography (for example, a textured surface) can be imparted into or onto a balloon prior to inflation. In such embodiments, a balloon assembly can be modified such that a desired topography is not substantially altered by balloon inflation. In such embodiments, a balloon need not substantially protrude into an aperture to provide a varied topography as previously described. Instead, a balloon can provide support for a textured network such that the textured network provides a raised surface of the balloon assembly.

In various embodiments, a balloon can be covered and/or wrapped with a textured network that provides a topographical feature. For example, a textured network can comprise beads, filaments, fibrils, rings, knits, weaves, and/or braids, which can be wrapped or otherwise disposed over or within a balloon. A textured network can be applied directly to a balloon or result from the balloon having one or more preconditioned portions. The textured network can be used to alter the topography of the balloon. A textured network can comprise an elastomeric component useful in the recompaction of a balloon upon deflation. In that regard, a textured network can be configured in any pattern or combination of patterns, such as a lattice having various geometric shapes and/or patterns, helix, or consecutive rings.

Figure 13A:
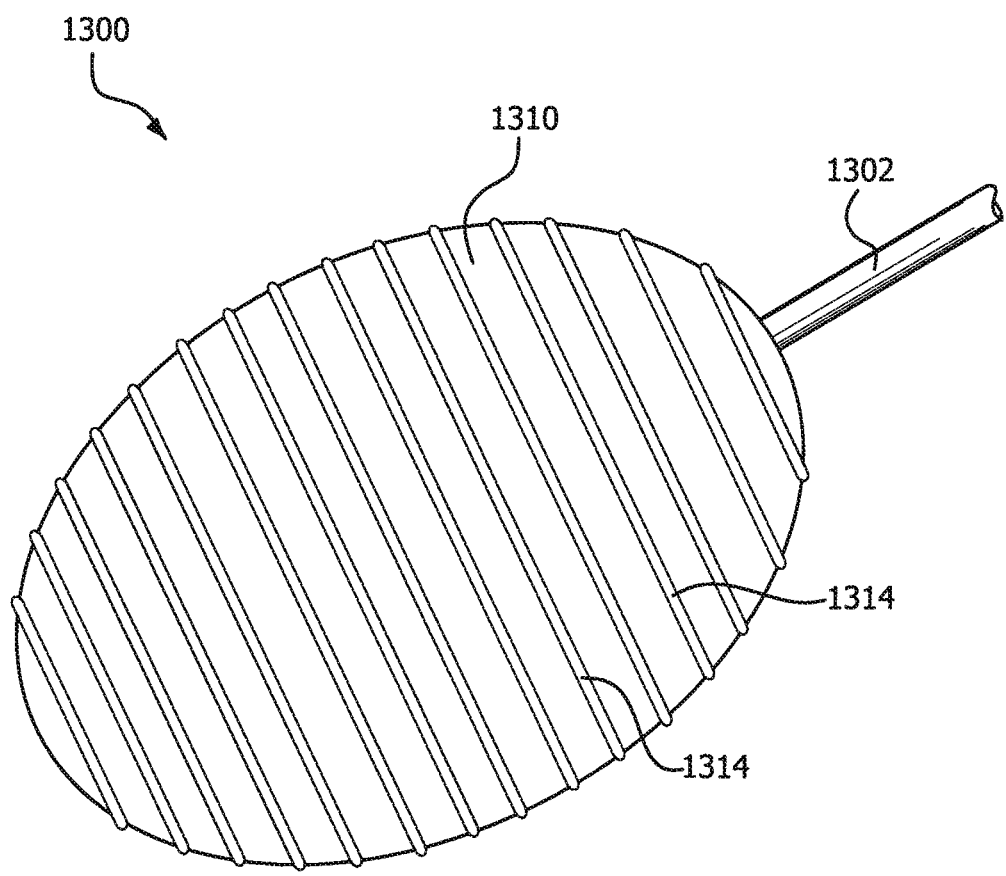
FIGS. 13A to 13C illustrate a textured balloon assembly in accordance with various embodiments.
Figure 13B:
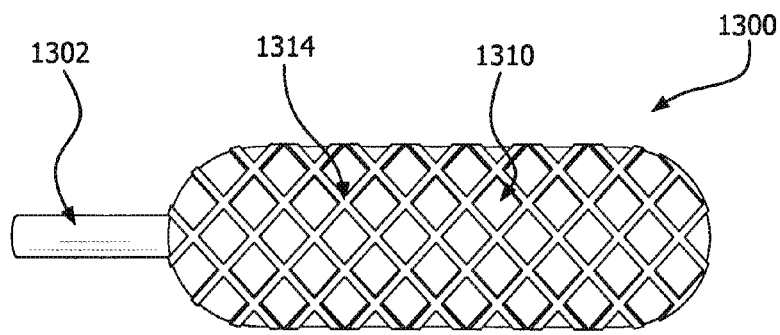
Figure 13C:
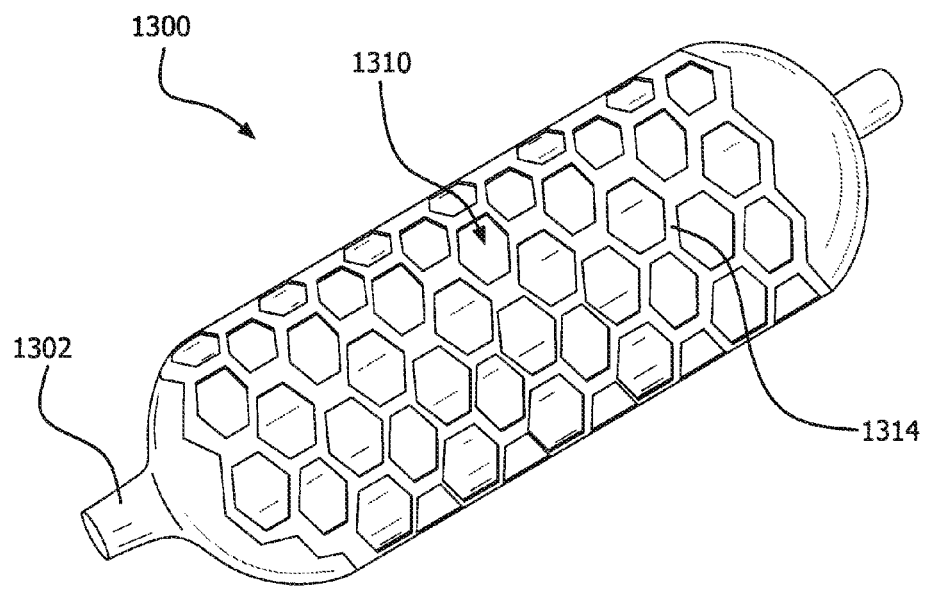

With reference to FIG. 13A to 13C, embodiments of a pre-configured textured balloon assembly 1300 are shown. Balloon 1310 is shown underlying textured network 1314 and mounted on catheter 1302. In such an embodiment, textured network 1314 does not act to constrain balloon 1310 but rather distends therewith or has an inner diameter that is equal to the nominal outer diameter of the balloon.

Textured network 1314 can be formed in a variety of ways. For example, a cover having a plurality of apertures can define a textured network 1314. Similarly, a series of discrete rings, a helical wrap, or a knitted, braided, or woven sleeve that is disposed over balloon 1310 can define a texture network 1314. FIG. 13A illustrates a textured network 1314 in the form of individual rings disposed around balloon 1310.

In other embodiments, balloon 1310 can be covered with a knitted, woven, and/or braided sleeve, such as a knitted tubular form to define textured network 1314. Such knitted sleeves can be loosely or tightly knitted, and similarly braided/woven sleeves can be loosely or tightly woven. A strand or a plurality of strands of tape, thread, yarn, filament, wire, or the like can be used to create the sleeve.

A variety of factors of the knitted sleeve can be controlled to control the properties of textured network 1314, e.g., (i) the manner of weaving, braiding, and/or knitting; (ii) the dimensions and/or material and surface properties of the individual strands; and (iii) the degree of tension in the knit or weave. Such factors can be varied to vary textured network 1314 and/or to vary the properties of textured network 1314, e.g., the elasticity of network 1314. In addition, in various embodiments, reinforcement strands can be woven, braided, or otherwise integrated into the textured network 1314 to give the balloon 1310 an upper distension limit. Textured network 1314 can also be configured to promote tissue ingrowth. Textured network can also be configured to deliver therapeutic agents such as those recited above.

Reinforcement strands can be comprised of any suitable biocompatible material that can be formed into a flexible strand. Strands can be a metallic, polymeric, or composite material. Strands can be elastic or inelastic. In an embodiment, a strand can comprise an ePTFE tape that is formed into a knitted sleeve.

The knitted sleeve can be wrapped with ePTFE film such that the ePTFE film is at least partially within the knitted ePTFE.

Textured network 1314 can be formed from wires, thermoplastic filaments or rings. As shown in FIG. 13A, textured network 1314 can comprise a thermoplastic polymer, e.g., fluoro ethylene propylene (FEP). Forms of ePTFE such as urethane imbibed ePTFE can be used as well.

Optionally, a sleeve or tube can be thermally bonded to an underlying or overlying film material in order to bond or integrate textured network 1314 to balloon 1310. For example, an outer film can be wrapped over textured network 1314. The assembly can be subjected to thermal treatment at about 380° C. for 15 minutes to facilitate bonding. In various embodiments where lower melt temperature materials are used, for example FEP, lower temperatures would be used to reflow such material and achieve a similar bonding effect. The distal end can be crimped and wrapped with a sealing film. The proximal end can be adhered to a catheter using adhesive.

Figure 13D:
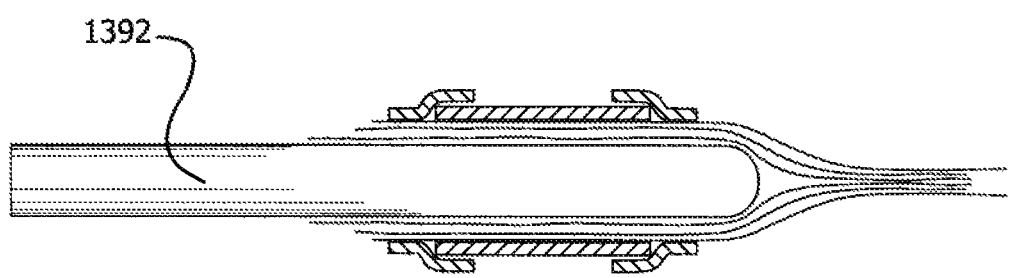
FIG. 13D illustrates a cross sectional view a textured balloon assembly on a mandrel, in accordance with various embodiments.

With reference to FIG. 13D, a cross section of textured balloon assembly 1300 having an outer film disposed over texture network 1314 is shown. Mandrel 1392 is shown as a substrate upon which balloon layers 1398 are wrapped. Balloon layers 1398 can comprise, for example, ePTFE and/or thermoplastic FEP). Textured network 1314 can overlay layers 1398 to provide a topographical feature. Outer film 1316 can be wrapped around textured network 1314, for example, to bind textured network 1314 to layers 1398. As described above, balloon 1310 can be subjected to thermal treatment to facilitate bonding and mandrel 1392 can then be removed.

With reference again to FIGS. 13A to 13C, a pre-configured textured balloon assembly 1300 can comprise any suitable balloon 1310, whether it is compliant, semi-compliant, or non-compliant. Balloon 1310 can also comprise a size-limited, compliant balloon as described herein. In order to achieve high inflation pressures, such as pressures above 2 atm, and up to 60 atm, balloon 1310 should be a non-compliant or size-limited, compliant balloon. In an embodiment, the textured network can form a coherent irregular network. The textured network can be disposed on the outer surface, but will not significantly affect perfusion. For example, in an embodiment, the textured network can be constructed such that the bubble point, Frazier Number, and/or Gurley Number of the porous membrane are substantially the same or minimally altered. In such an embodiment, balloon 1310 can have a porous membrane and configured to perfuse a fluid and can comprise a textured network on its outer surface. The network can be formed from thermoplastic elements. U.S. Patent Publication No.

2012/064273 by Bacino entitled "Porous Article" is hereby incorporated by reference in its entirety for purposes of describing a coherent irregular network and various techniques for applying the network to the balloon's outer surface. Some of the details of the Bacino publication are described below.

In an embodiment, the coherent irregular network that may be attached to the underlying balloon 1310 or made into a free standing article as defined herein is a coherent irregular network of thermoplastic particles attached together. The term coherent as used in defining the coherent irregular network means that the article comprises elements effectively connected together such that the article can be free standing, and therefore does not include discrete particles that may be attached to a substrate, such as fluoroplastic adhesive coated onto a expanded fluoropolymer substrate. The term irregular as used in defining the coherent irregular network means that the structure of the coherent irregular network comprises connecting portions that do not have a consistent diameter or cross-section area across along the length of the connecting portions between intersections or attachments with other connecting portions, particles or elements, and therefore does not included spun-bonded, woven, or felted products that consists of fibers having a consistent cross sectional area. The term network as used in defining the coherent irregular network means that individual elements of the coherent irregular network are effectively attached together to provide a contiguous structure. The coherent irregular network is further defined as comprising porosity between the attached elements throughout the thickness such that the coherent irregular network is porous and permeable. The coherent irregular network is still further defined as having open areas.

A wide range of thermoplastic particles could be used to create the coherent irregular network, including particles having a high molecular weight, or low melt flow index (MFI). Particles with MFI values between 0.2 and 30 g/10 min when tested according to the MFI method described herein may be more desirable. However particles with MFI values greater than 0.1 or less than 50 g/10 min may also be used. In addition, fluoroplastic particles including but not limited to FEP, EFEP, PFA, THV, PVDF, CTFE, and the like, and mixtures thereof are desired in some applications.

In an embodiment, the coherent irregular network is attached to balloon 1310, e.g., the porous membrane of balloon 1310, and has a surface roughness defined by a Sp value of at least 35 µm. The size, type, and blend of the particles can be selected to get a desired degree of surface roughness. In addition, using two or more different types of particles can aid in attaching the coherent irregular network to the expanded fluoropolymer layer, attaching the permeable layer to a support layer, or provide a desired permeability, porosity, surface area, abrasion resistance, surface roughness, free standing film strength, or electrical conductivity or the like.

The coherent irregular network disposed on at least a portion of the outer surface of balloon 1310 can comprise attached thermoplastic elements that have been fused together creating a network having connecting portions, porosity, and open areas. Open areas as used herein are defined as areas of porosity in the coherent irregular network that extend completely through the thickness of the material. The coherent irregular network does not completely occlude the surface of the underlying porous membrane, and the areas where the porous membrane can be identified through the coherent irregular network are open areas. The "size" of an open area as used herein is defined as being the distance of the longest straight line that can be drawn across the open area. Upon inflation of the balloon, the size of the open area can increase in size as the elements of the textured network become separated. This increase in size can further increase the "grittiness" of the balloon.

In one embodiment, the coherent irregular network further comprises non-melt processible particles. The nonmelt processible particles may be inorganic particle, such as silica, carbon, and the like, or a non-melt processible polymer such as polyimide, PPS, PTFE, or the like. In these embodiments, the thermoplastic particles or elements are attached to create a coherent irregular network, and the non-melt processible particles are attached therein or thereon.

In accordance with the above description, in an embodiment, a balloon assembly can comprise a balloon having a porous membrane having an outer surface and configured to perfuse a fluid, a template having at least one aperture about which a protrusion can distend, and a textured network disposed on at least a portion of the outer surface of the balloon and comprising a plurality of voids. The textured network can be a coherent irregular network of thermoplastic elements. In addition, the portion of the outer surface of the porous membrane can comprise an Sp value of at least 35 µm.

In an embodiment, balloon 1310 can comprise an ePTFE wrapped balloon. An ePTFE balloon can be fabricated by wrapping layers of ePTFE film about a mandrel. Wrapping can be a helical or longitudinal wrap. The ePTFE balloon can be subjected to thermal treatment at about 380° C. for 15 minutes to facilitate bonding and one end crimped. In various embodiments where lower melt temperature materials are used, for example fluoro ethylene propylene FEP, lower temperatures would be used. Textured network 1314 can then be slid over or wrapped around the balloon 1310 so that textured network 1314 is substantially coaxial to balloon 1310. Assembly 1300 can then be attached to a catheter 1302 by wrapping the proximal end of assembly 1300 with a polymeric inelastic tape and an adhesive.

It should be noted that the present disclosure contemplates a balloon assembly comprising a pre-configured texture balloon as described combined with a template having at least one aperture. For example, a ribbed balloon can form a protrusion about an aperture. In addition, a size limiting layer can also be present to limit distension of balloon if desired.

In various embodiments, portions of a template or balloon cover can be scored, etched, or otherwise partially cut or weakened. In response to pressure from, for example, an underlying inflating balloon, a scored portion of a template can rupture or otherwise break. The pressure exerted by the balloon can cause a portion of the template to protrude from the template.

In various embodiments, the protruding portion can be configured to be sharp by selectively shaping the scored portion. For example, a triangle shape can be formed and scored at one apex. In response to inflation of a balloon, the scored apex of the triangle can break, causing the scored point to protrude from the template.

The point (or other resulting shape) can be directionally oriented relative to the tissue. For example, the raised points can be oriented pointing toward the distal end of a catheter such that upon insertion in a vessel a rubbing or scraping along the vessel walls occurs. Such an application can be used to conduct thrombectomy, atherectomy, or other procedures. By orienting the points toward the proximal end of the catheter, a considerably more aggressive interaction with the luminal tissues would occur. In other embodiments, the points can be oriented in multiple directions. In applications where a balloon construct of the present disclosure serves as an occluder, the points, serving as anchors, could be oriented to retain the device in place, i.e., against the direction of blood flow or motion of the surrounding tissue(s). Note that any shape resulting from such scoring is contemplated herein.

Figure 14A:
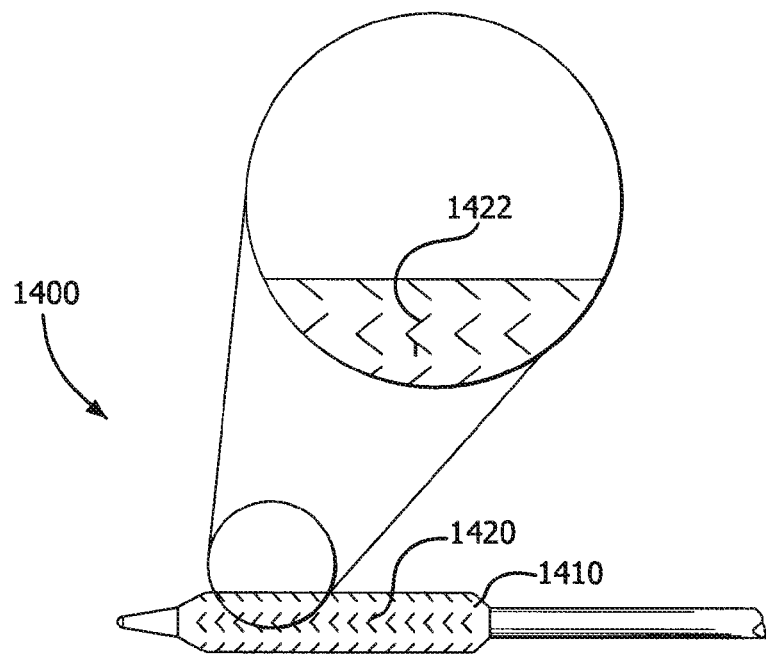
FIG. 14A illustrates a deflated balloon assembly with a scored template pattern from an exterior perspective, in accordance with various embodiments.
Figure 14B:
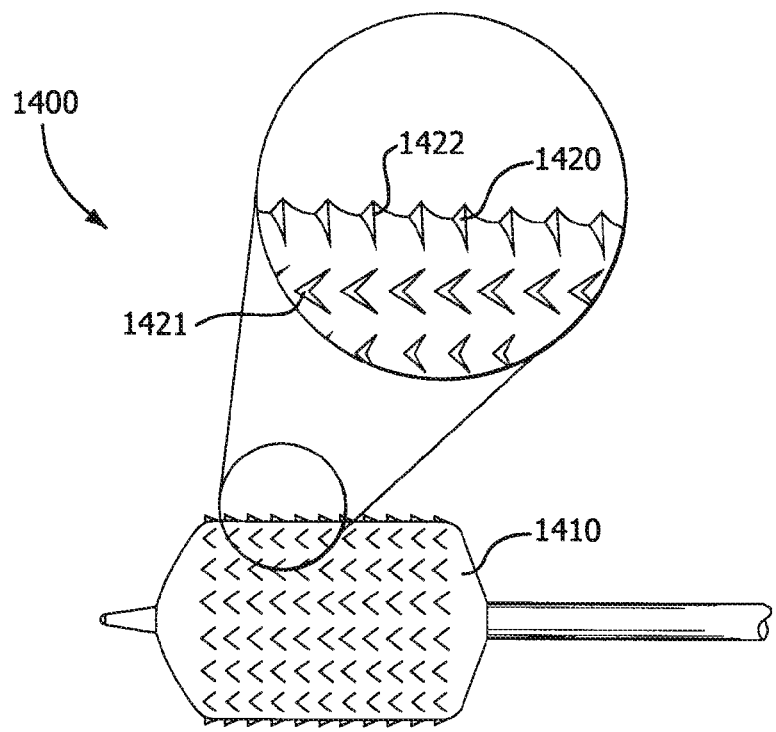
FIG. 14B illustrates an inflated balloon assembly with a deployed scored template pattern from an exterior perspective, in accordance with various embodiments.

Accordingly, in an embodiment, balloon assembly can comprise balloon and an template overlying at least a portion thereof which comprises a surface that is disrupted upon inflation. For example, with reference to FIGS. 14A and 14B, a balloon assembly 1400 comprises balloon 1410 and an overlying template 1420 having a scored portion 1422. Upon inflation, as illustrated in FIG. 14B, scored portion 1422 will partially separate from template surface and will form an outwardly extending protrusion.

In an embodiment, the ruptured portion of template 1420 that is created by the rupture of score 1422 is aperture 1421 in which balloon 1410 can be at least partially exposed. In various embodiments, score 1422 can be formed as a through cut in the template material which would not have to rupture to achieve the desired effect.

As illustrated, scoring and later rupturing of scores can enable the insertion of sharp objects into the body in a substantially unsharpened state and then provide for the deployment of the sharp object at a particular time. In addition, scoring and later rupturing can aid in the delivery of therapeutic agents. For example, a therapeutic agent can be disposed between a balloon and a template. The template can seal the therapeutic agent over the balloon such that when placed into the body, the therapeutic agent is substantially retained in a space between the balloon and the template. Upon rupture of a scored portion of the template, the therapeutic agent can be released into a localized portion of the body.

Similarly, in another embodiment, with reference to FIGS. 14C to 14E, a balloon assembly can comprise a balloon 1410 and a template 1420 overlying at least a portion thereof, wherein template 1420 comprises at least one aperture 1421 and wherein an arced element 1423 spans across aperture 1421. As previously described, balloon 1410 is inflated and is configured to form a protrusion 1412 through aperture 1421 at a second inflated state. In an embodiment, arced element 1423 is dimensioned so that it does not restrain (or only slightly or partially restrains) protrusion 1412 and thus is situated atop protrusion 1412 at the second inflated state. Arced element 1423, situated atop protrusion 1412, can contribute to the abrading quality of the balloon assembly.

Arced element 1423 can comprise an inner arc edge having an arc length, wherein the arc length of the inner arc edge is similar to the arc length of the protrusion that protrudes through the aperture so that the inner edge lay atop protrusion 1412. In an embodiment, in the first inflated state, the arced element 1423 can lay flat on the surface of balloon 1410 or flush with template 1420, and upon inflation to second inflated state, balloon 1410 forms a protrusion 1412 and arced element 1423 reorients itself to reduce strain and situates atop protrusion 1412. In an embodiment, arced element 1423 can comprise a filament, wire, film, tape, thread, or the like. In addition, arced element 1423 can be integral with template 1420, i.e., cut into the template pattern or be attached thereto. FIGS. 14E(1) to 14E(4) illustrate various arced element 1423 patterns.

In an embodiment, with reference to FIGS. 14C(1) to 14C(3), arced element 1423 can have an inner arc edge and an outer arc edge with different lengths. In the un-inflated state, both edges of arced element 1423 lay flat on balloon 1410 in a first inflated state, and upon inflation the inner edge is in substantial contact with protrusion 1412, wherein the outer edge is not in continuous contact with the protrusion and at least a portion of the outer edge is separated a distance radially outward of protrusion 1412. Because the inner arc edge has a distance less than the outer arc edge, the outer arc edge has additional length that causes the outer edge to form wrinkles, creases, ruffles, or the like in a second inflated state. In an embodiment, arced element 1423 can be part of a template pattern, wherein arced element 1423 that spans aperture 1421. In other embodiments, with reference to FIGS. 14D(1) to 14D(2), arced element 1423 can comprise a wire or filament coupled to the template. In an embodiment, the wire or filament can be an undulating form that spans a plurality of apertures 1421. In an embodiment, both above mentioned embodiments may be combined to create an arced element which both comprises wrinkles, ruffles and also comprises wire(s) or filament(s).

Figure 15:
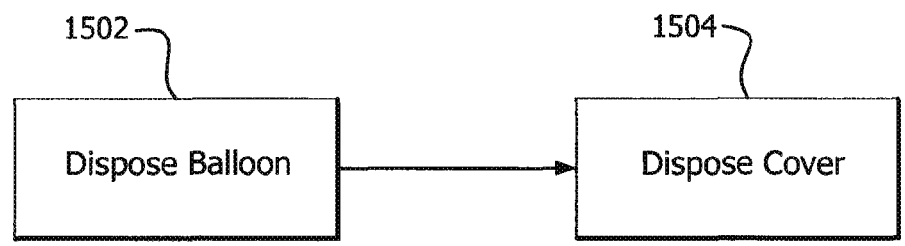
FIG. 15 illustrates a method of making, in accordance with various embodiments.

Various embodiments of the herein disclosed balloon assemblies can be constructed in any suitable manner. For example, as shown in FIG. 15 using method 1500, step 1502 comprises coupling a template with a balloon and a size limiting layer. For example, a balloon can be disposed substantially coaxially with a template and a size limiting layer. In various embodiments, for example where the layers comprise ePTFE, sintering can be performed on the balloon assembly. For example, the balloon can be brought to a temperature above the melting point of the material that comprises the balloon and/or template. Sintering in this manner can produce bonding of ePTFE layers. Step 1504 can comprise disposing a balloon on a catheter. Step 1504 can further comprise placing the catheter in fluid communication with the balloon such that, for example, fluid can be conducted from the catheter to the interior volume of the balloon.

Figure 16:
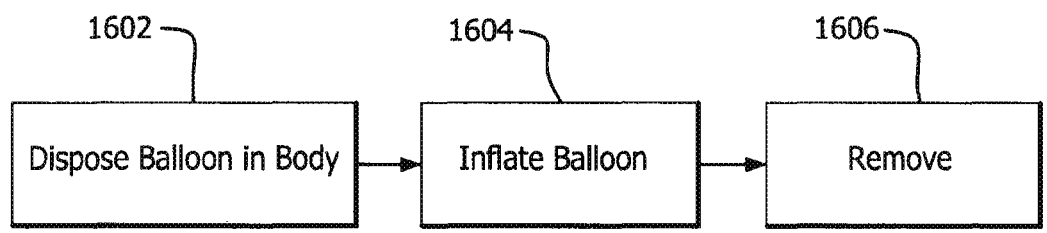
FIG. 16 illustrates a method of use, in accordance with various embodiments.

In various embodiments, method 1600, as shown in FIG. 16, for using a balloon assembly can be used. Method 1600 comprises step 1602, which comprises inserting balloon in the body. Any portion of the body or a lumen of the body can be used in step 1602. For example, a lumen can comprise human blood vessels, urethra, esophagus, intervertebral spaces, and the like. Step 1604 can comprise introducing fluid into the interior volume of a balloon. Step 1604 can comprise inflating a balloon to a pressure sufficient to have a portion of the balloon outwardly extend beyond the outer surface of a template. Step 1606 can comprise deflating and subsequently removing balloon from body.

In various embodiment, the balloon assembly with a template can comprise a plurality of apertures located along a length of the assembly (and optionally about a circumference) and can be used for locating a side branch vessel. Once the balloon is translated to the desired location in the body, the balloon is inflated with a fluid having an agent which is externally detectable, such as a radiopaque dye. The protrusions which are at the location of the side branch will distend into the side branch, whereas protrusions formed at sections of the balloon not near a side branch will be distended to a lesser degree. Thus, the side branch is visible by way of the protrusions therein.

In various embodiments, a balloon assembly can be configured to have an abrasive topography. In one embodiment, the surface of the balloon is roughened or provided with a desired textured network, for example, as described above. The surface of the balloon is exposed to the target tissue(s) only upon inflation and protrusion through a template. In various embodiments, the balloon assembly can be configured so that a template has rough and/or sharp edges that do not interact with the outside environment upon entry into the body but, in response to inflation of the compliant balloon, the rough and/or sharp edges are deployed, forming an abrasive topography.

In various embodiments, a varied topography balloon or a pre-configured textured balloon assembly can be constructed using multiple layers of material, such as ePTFE, nylon and/or elastomers on either or both the balloon or the template. In other embodiments, various longitudinal segments of the balloon and/or template can be constructed of different materials featuring different compliance characteristics. Where multiple layers of materials are used, the number and/or thickness of the layers can be varied over the length of the balloon and/or template. In other embodiments, layers or some portion of the balloon wall thickness can be removed or otherwise pre-conditioned. Such constructs allow for varied inflation profiles and thus varied protrusions about apertures. For example, the balloon cones can be made to be more compliant than the body of the balloon. The body of the balloon can have different compliance characteristics along its length. Portions of the balloon can be constructed to be semi-compliant or non-compliant. Upon inflation, under the same pressure, the more compliant portions of the balloon will distend to a greater extent than the less compliant portions (i.e., form a height gradient).

Optionally, balloon assemblies as described herein can comprise a distal cap to secure the distal terminus of a balloon to catheter. A distal cap can be referred to as an olive. An olive can abut against the distal end of a balloon or catheter. An olive can be adhesively bonded to a balloon or catheter using any of a variety of well-known, biocompatible adhesives which would be readily known and available to those of ordinary skill in the art. Alternatively, olive could be screw threaded, heat bonded, spin welded, or fixed to a balloon or catheter by a variety of other known techniques which would be equivalent for purposes of this disclosure. Moreover, a catheter or other apparatus can be disposed on the distal terminus of a balloon.

In further embodiments, balloons assemblies disclosed herein can comprise size-limited, compliant balloons that perfuse in response to an increase in internal pressure.

In various embodiments, balloon assemblies disclosed herein are steerable when in both inflated and/or deflated states. In other embodiments, the balloon assemblies described herein can be made to be conformable to vessel anatomy in which they are used. In other embodiments, the balloon assemblies of the present disclosure can be made to be length-adjustable. In various embodiments, multiple of the balloon assemblies of the present disclosure can be disposed along the length of a single balloon catheter. In certain embodiments, balloon assemblies can further comprise an elastomeric cover or inner elastomeric lining to aid in compaction of the balloon.

In various embodiments, balloon assemblies disclosed herein can be used with a pressure retaining valve. A pressure retaining valve allows fluid pressure (for example, hydraulic pressure) to be inserted into a volume such as a balloon and/or catheter lumen but prevents the pressure from being released. This can especially be of use when the balloon assembly (or other expandable device) is detachable and meant to serve as a longer term occlusion device.

Without intent of limiting, devices disclosed herein (e.g., varied topography or textured balloon assemblies) are useful in any medical applications or treatments such as, for example, tissue ablation, angioplasty, cancer therapies, thrombectomy, embolectomy, angioplasty/stenting; angioplasty/stenting in the kidneys; angioplasty/stenting in blood carrying passageways; angioplasty/stenting in the legs; angioplasties of graft-artery anastomotic strictures; stenting used to aid attachment of endoprostheses such as gastrointestinal liners, cancer of the adrenal cortex; cancer of the endometrium; cancer of the larynx (voice box); cancer of the pancreas; cancer of the parathyroid; cancer of the thyroid gland; cancer of tissues of the lip or mouth (e.g.; tongue; gums; lining of cheeks; bottom of mouth; hard & soft palate; retromolar trigone); cancers; cancers of the blood; cancers of the nasal cavity; candidiasis; capsules; carcinoid syndrome; carcinoid tumors; cardiovascular disease (CVD); cardiovascular patches; carotid artery stenting (CAS); casts; catheters; cells; choriocarcinoma; chronic myeloid leukemia (CML); deep venous thrombosis (DVT); delayed release grafts; delayed release stent-grafts; delayed release stents; dialysis access applications; dialysis equipment; dialysis grafts; drug delivery devices; drug-eluting grafts; drug-eluting implants; drug-eluting sutures; drug-eluting stents; endoprosthesis stent-grafts; ostia ballooning, deployment of endoprosthesis in an ostia; endovascular aneurysm repair (EVAR); endografts; endovascular grafting; endovascular stent-grafts; endovascular therapy; esophageal stenting; eustachian tube dysfunction; iliac stents and stent-grafts; immunizations; infection (e.g. in the lungs; throat; sinuses; kidneys; bladder; abdomen; and skin); infections of female reproductive organs; infections of the urinary and lower respiratory tract; infections of throughout the body (septicemia); inflammatory bowel disease (e.g., Crohn's disease); interatrial defects; influenzas; injuries; insomnia; internal thoracic artery grafts (ITA, mammary artery); intestinal stents; intestinal stent-grafts; locating a side branch; medical devices; modified release stent-grafts; modified release stents; nephroureteral stenting; neurological devices; pancreatic stenting; pancreatic cancer; pancreas; pancreatitis; percutaneous angioplasty of Takayasu arteritis; penile implants; peripheral vascular stents and stent-grafts; positioning in urethral lumen; pulmonary conditions; radial artery grafts; rectal stents and stent-grafts; reduction or shrinkage of aneurismal (sac); regrow nerve fibers or organs; reinforce collapsing structures; renal cell cancer; renal cell carcinoma (RCC) tumors; renal impairment; renal grafts; renal stents and stent-grafts; renal transplants; renal transplants; repair of aneurysms; repair of living cells; tissues or organs; stenosis of the renal artery (e.g., at ostium); stent-grafts; stenting; stents; stents in femoral arteries; surgical procedures; sustained released grafts; sustained release stent-grafts; thoracic aneurysm repair; thrombosis; thrombotic conditions; treatment of other diseases, cells, tissue, organs, bones, referenced in Gray's Anatomy and disorders (herein incorporated in its entirety as a reference); or combinations thereof, for example.

In various embodiments, balloon assemblies of the present disclosure can be used in conjunction with drug eluting or drug delivery balloons. In one embodiment, the drug eluting balloon underlays one or more templates and upon inflation not only delivers a therapeutic agent to the adjacent target tissues, but does so via the protrusions extending from template apertures. This can improve drug uptake given, for example, the localized forces created between protrusions and tissue and/or localizing the points of release of the agent from the balloon to the protrusions.

When used to place, size, or "touch up" stents or stent grafts (or other endoprostheses), a varied topography or textured balloon of the present disclosure can be constructed so as to provide enhanced stent retention, stent deployment, and stent release.

For example, the protrusions formed by the template(s) can be of any shape, size, surface texture and/or material to adhere to or prevent slippage of the balloon and inner walls of such prostheses. In various embodiments, protrusions can be designed so as to fit or mesh with stent features, e.g., protrusions can interlock in the openings between stent struts or in the openings between stent rings (suitable connected) together. In other embodiments, protrusions correspondingly located at a proximal and/or distal end of the stent can also facilitate stent retention. This makes their tracking and placement easier and more accurate. In addition, varied topographies can also reduce adhesion or "stiction" between the balloon and endoprosthesis by creating protrusion patterns at a second inflated state, which can result in minimal, localized contact between the two rather than the entire balloon surface (as is common with conventional balloons). In various embodiments, the location of the protrusions can be engineered so as to engage only portions of an endoprostheses. Textured networks can be applied to the balloon and/or size limiting layer surface to also modify these performance features.

Figure 20A:
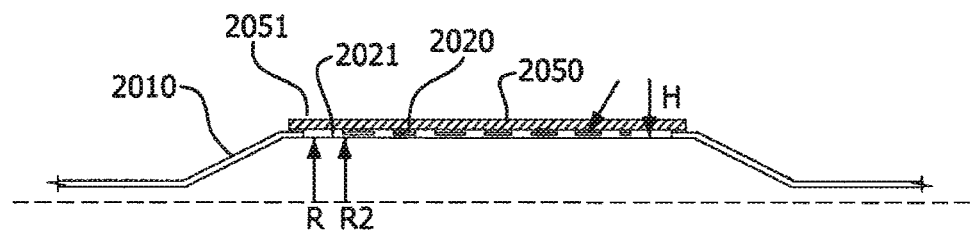
FIGS. 20A-20B illustrates a varied topography balloon assembly with a stent device mounted thereon, the stent device having deployable anchors which are actuated by protruding apertures.
Figure 20B:
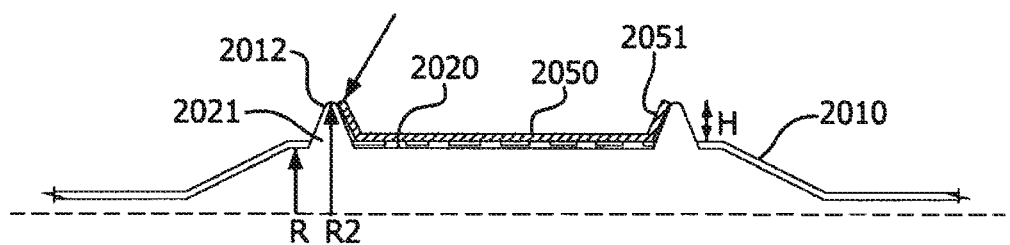

In one embodiment, with reference to FIG. 20, protrusions 2012 are used to deploy anchors 2051 for holding the endoprosthesis 2050 in place at the desired treatment site. Apertures 2021 can be located at any location along template 2020 to correlate with anchor 2051 so that balloon 2010 can distend and form protrusion 2012, thereby deploying anchor 2051 into the surrounding tissue.

Figure 21:
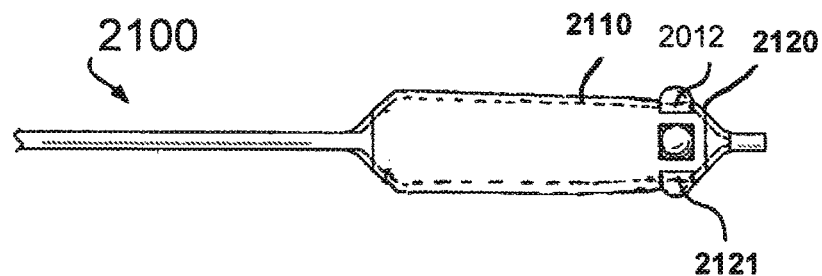
FIG. 21 illustrates a varied topography balloon assembly wherein an aperture or a plurality of apertures are located on a circumferential section.

Similarly, the aperture and/or protrusions pattern can be designed for purposes of ostia ballooning, flaring a stent end(s), and/or deploying a flange. In an embodiment, with reference to FIG. 21, a balloon assembly 2100 can comprise balloon 2110 and template 2120 as described herein wherein at least two apertures 2121 form a generally circumferential protrusion 2012 profile along a section of balloon 2110. This section can be located at a proximal and/or distal end of assembly.

With regard to application of these balloon constructs to angioplasty, it will be understood that they offer several clinical advantages. Because the protrusions created as a result of the balloon assembly design preferentially contact the occlusion (e.g., plaque), there are distributed stress concentrations created over the surface of the occlusion. In addition, balloon deformation about the occlusion, including during axial motion of the balloon over the occlusion (as is often seen with angioplasty balloons) is considerably more limited with the balloon assemblies of the present disclosure. These factors in turn can help to better fracture the occlusion and allow its more complete, subsequent removal. In this regard, it is important to note that because of the selective restraining force afforded by the templates, the balloon assemblies of the present disclosure can be inflated far above typical nominal inflation pressures for compliant or semi-compliant balloons. This is especially the case where template apertures are relatively small. Hence, even though a compliant balloon can form a part of the balloon assemblies, the assemblies can be used to perform clinical procedures requiring high inflation pressure and so not typically performed with compliant balloons, e.g., angioplasty.

Additionally, in various embodiments, the protrusions resulting from designs made in accordance with the present disclosure can be used in the visualization of anatomical structures. The balloon can be filled with a visualization (e.g., contrast) agent. Upon inflation, the protrusions will be distinctly visualized (e.g., via fluoroscopy). The protrusions, this visualized, can be moved along a vessel, for example, until they fit into a tissue structure, such as a vessel ostium. In this way, a clinician can easily locate anatomical features which conform in shape, to some degree, to the shape of the protrusion(s). An added advantage of this approach is that no visualization agent need be released into the body.

Another clinical advantage offered by the present disclosure is that balloons can be constructed so as to expand protrusions to pre-determined heights, both final expanded heights and heights during expansion. This "progressive protrusion" can be clinically useful. This can be done by engineering the design of the balloons to correlate with inflation pressures and/or inflation fluid volumes. This provides clinicians with variable control during use of these devices.

As noted above, further clinical advantages are offered by the present disclosure in that a topographically-variable balloon used can provide increased surface area to prevent acute migration of the balloon and/or encourage tissue ingrowth and/or thrombogenesis. This can be beneficial in balloon assemblies used as occluders.

In addition, balloon assemblies in accordance with present disclosure can be used to "scrub" or otherwise displace or remove thrombus or plaque in the vasculature. A coarse or textured topography can be helpful in enhancing engagement of the balloon assembly with the thrombus or plaque and/or helpful in occluding a blood vessel. For example, balloon assemblies in accordance with the present disclosure can be used in conjunction with a reverse blood flow system like those used in carotid artery stenting. In such reverse blood flow systems, balloon assemblies in accordance with present disclosure can be used to occlude the external carotid artery and/or the common carotid artery. Balloon assemblies in accordance with present disclosure can provide enhanced occlusion characteristics relative to conventional balloon assemblies.

In addition, balloon assemblies in accordance with present disclosure can be used as a balloon anchored introducer in a stenting procedure. A balloon assembly can be positioned in the body distal to the desired stent site. The balloon assembly can then be inflated to anchor the balloon assembly and thus provide support for a guidewire or other apparatus that can deliver and deploy a stent to the desired stent site. Balloon assemblies in accordance with present disclosure can provide enhanced anchoring characteristics relative to conventional balloon assemblies.

The following example details how an exemplary balloon of the present disclosure was constructed.

Example 1: Method of Making the Template with Apertures

An ePTFE film was obtained of the general type as disclosed in U.S. Pat. No. 7,306,729. A discontinuous layer of the thermoplastic FEP (fluoro ethylene propylene) was applied to one surface and the film was slit into a tape. The tape was wrapped around a 6 mm mandrel so that the film's machine direction was oriented about the circumference of the mandrel. A length of tape was wrapped that resulted in approximately 18 layers of film. The tape-wrapped tube was thermally treated in an oven at 320° C. for 12 minutes. The film tube was removed from the oven and then removed from the mandrel and cut to 80 mm in length.

The 6 mm tube was placed over a suitable mandrel and square apertures measuring 2 mm by 2 mm were cut through the tube using a CO2 laser, leaving 1 mm of film material between apertures. Six rows of apertures were cut about the circumference of the tube, parallel to the tube's longitudinal axis. The pattern was cut over a 60 mm length centered in the 80 mm tube. This tube is referred to as a "template" with "apertures."

Example 2: Method of Making a Balloon Assembly Comprising a Size Limiting Layer Overlaying a Compliant Balloon, Both of which are Circumscribed by a Template with Apertures An ePTFE film was obtained of the general type as disclosed in U.S. Pat. No. 5,476,589, entitled, "Porous PTFE Film And A Manufacturing Method Therefore," which issued Dec. 19, 1995. The film was cut into a tape of 25 mm width and helically wrapped about a 9 mm stainless steel mandrel at an 11.4 mm pitch. The wraps were repeated on a bias in opposite directions to produce an approximately 4-layer film tube.

This tube was then thermally treated in an oven at 380° C. for 9 minutes and then removed from the oven. The tube was removed from the mandrel, placed over a 7 mm mandrel and axially stretched to decrease its diameter to 7 mm. A sacrificial ePTFE tape was helically wrapped over the film tube on the 7 mm mandrel.

The tube assembly was then axially compressed to 85% of its original length. The tube assembly was then subjected to thermal treatment at 380° C. for 1 minute and then removed from the oven. The sacrificial ePTFE layer was removed and discarded. The 7 mm tube construct was cut to an 80 mm length. This tube can be referred to as a "size limiting layer".

A compliant polyurethane balloon catheter was obtained with a balloon having a diameter of 10 mm and length of 60 mm ("COAX," Bavarian Medizin Technologies (BMT), Germany).

The size limiting layer was slid over the balloon assembly (with the balloon in its collapsed state). The ends of the size limiting layer were secured to the catheter using LOCTITE adhesive 4981 (Henkel Corporation, Dusseldorf, 40589 Germany) applied to a 6 mm wide ePTFE tape as it was wrapped 5 times about the size limiting layer tube ends. The balloon was then inflated to an approximate 5 mm diameter.

The template layer, as described in Example 2, was slid over the size-limiting layer and the compliant balloon (with the balloon at its 5 mm diameter). The ends of the template layer were secured to the catheter using LOCTITE adhesive 4981 applied to a 6 mm wide ePTFE tape as it was wrapped 5 times about the tube ends. The balloon was then inflated to an approximate 6 mm diameter.

The balloon assembly was then inflated to 4 atmospheres and protrusions of the underlying compliant balloon were noted extending from the apertures.

Example 3: Method of Making a Balloon Assembly Comprising a Size Limiting Layer Overlaying a Compliant Balloon, Both of which are Circumscribed by a Template with Apertures Having a First Distension Profile and a Second Distension Profile In order to form a distensible template, construct a helically wrapped 8 mm film tube using an ePTFE film as described in U.S. Pat. No. 7,306,729, issued Dec. 11, 2007. Laser cut the 8 mm film tube to form 2 mm×2 mm openings. Reduce the template diameter by stretching the template in a longitudinal direction until the inside diameter of the template reaches approximately 4 mm. Insert a 4 mm mandrel into the 4 mm drawn down template. Over wrap the template on the 4 mm mandrel with a sacrificial film. Longitudinally compress (or scrunch) the over-wrapped template to approximately 60% of the original length. Bake the compressed template at 380° C. at a time ranging from (0 sec. to 120 sec.). This step sets the load at which the template will begin to distend. The lower the baking time, the smaller the load required to distend. Once set, remove the sacrificial film and the template from the 4 mm mandrel.

Obtain an inflatable, compliant balloon element constructed to be 8 mm×40 mm with a working length of 40 mm, two shoulders of length of 4 mm, and two seals of 7 mm, giving it an overall length of 62 mm.

Place an 8 mm×62 mm size limiting layer (constructed in a similar manner as described in Example 2) that has also been drawn down to 4 mm on a 4 mm mandrel. Cut the template to a length of (24 mm+7 mm to form the attachment to the size limiting layer at the seal), giving it an overall length of 31 mm. Slide the cut template over the size limiting layer that is on the 4 mm mandrel so the inside end of the template aligns with the center line of the size limiting layer. Wrap approximately 5 to 20 layers of a porous, sintered, sufficiently thin and strong ePTFE film, ½" wide using 4498 LocTite glue to adhere the template at center line of the size limiting layer. Remove the size limiting layer with the template attached from the 4 mm mandrel.

Place the 4 mm template and size limiting assembly over the compacted 8 mm balloon and secure both the proximal and distal ends (7 mm each) by wrapping approximately 10 or more layers of a porous, sintered, sufficiently thin and strong ePTFE film and 4498 LocTite adhesive around each end of the cover and catheter.

In another embodiment, a frangible template can be constructed as described in Example 3, instead using an ePTFE film as described in U.S. Pat. No. 5,814,405 Branca et al., which is hereby incorporated by reference in its entirety.

It will be apparent to those skilled in the art that various modifications and variations can be made in the present disclosure without departing from the spirit or scope of the disclosure. For example, while embodiments of the present disclosure have been described with reference to the inferior vena cava, embodiments are scaleable and applications in various central and peripheral vessels and lumens are contemplated herein. Additionally, the embodiments can be used in connection with not just humans, but also various organisms having mammalian anatomies. Thus, it is intended that the embodiments described herein cover the modifications and variations of this disclosure provided they come within the scope of the appended claims and their equivalents.

Benefits, other advantages, and solutions to problems have been described herein with regard to specific embodiments. However, the benefits, advantages, solutions to problems, and any element or combination of elements that can cause any benefit, advantage, or solution to occur or become more pronounced are not to be construed as critical, required, or essential features or elements of any or all the claims of the disclosure. Many changes and modifications within the scope of the instant disclosure can be made without departing from the spirit thereof, and the disclosure includes all such modifications. Corresponding structures, materials, acts, and equivalents of all elements in the claims below are intended to include any structure, material, or acts for performing the functions in combination with other claim elements as specifically claimed. The scope of the disclosure should be determined by the appended claims and their legal equivalents, rather than by the examples given above.

What is claimed is:

1. A balloon assembly comprising:
   a compliant balloon having an inflated configuration and a first upper distension limit; and
   a film template integral with the compliant balloon and comprising a high-strength expanded polytetrafluoroethylene (ePTFE) and having an outer surface, the film template extending along at least a portion of a working length of the compliant balloon and along at least a portion of a shoulder of the compliant balloon, the film template having a fixed upper distension limit and being inelastic in a direction transverse to a longitudinal axis of the balloon assembly;
   wherein the film template includes at least one aperture,
   wherein the film template is attached to a catheter,
   wherein the compliant balloon outwardly extends about the at least one aperture relative to the outer surface of the film template in the inflated configuration, and
   wherein the first upper distension limit of the compliant balloon is greater than the fixed upper distension limit of the film template.

2. The assembly of claim 1, further comprising a size limiting layer which is disposed around at least a portion of the compliant balloon.

3. The assembly of claim 2, wherein the size limiting layer comprises at least two layers of a helically wrapped polymeric tape.

4. The assembly of claim 2, wherein the size limiting layer comprises a high-strength ePTFE.

5. The assembly of claim 1, further comprising a therapeutic agent underlying the film template, wherein at least a portion of the therapeutic agent is conveyed out of at least one aperture upon the balloon extending through the aperture.

6. The assembly of claim 1, further comprising a secondary template disposed over the film template.

7. The assembly of claim 6, wherein the secondary template at least partially overlaps with the at least one aperture.

8. The assembly of claim 1, wherein the balloon is strained during inflation.

9. The assembly of claim 1, wherein the balloon comprises a first inflated state and a second inflated state, wherein at the first inflated state an outer diameter of the balloon is substantially equal to an inner diameter of the film template.

10. The assembly of claim 9, wherein the balloon comprises a substantially wrinkle free surface at the first inflated state.

11. The assembly of claim 1, wherein the film template comprises a rigid element.

12. The assembly of claim 11, wherein the balloon outwardly rotates the rigid element during inflation.

13. The assembly of claim 1, wherein a therapeutic agent is delivered through the balloon in response to an influx of fluid.

14. The assembly of claim 1, wherein the film template comprises a first aperture pattern and a second aperture pattern.

15. The assembly of claim 1, wherein the film template comprises a tape wrapped polymeric film.

16. A method of using the device of claim 1 in performing at least one of a thrombectomy, embolectomy, atherectomy, and angioplasty.

17. The assembly of claim 1, wherein the compliant balloon is attached to the catheter.

18. The assembly of claim 1, wherein the film template is attached to the catheter at a first end of the film template.

19. The assembly of claim 1, wherein the film template is attached to catheter at opposite ends of the film template.

20. The assembly of claim 1, wherein the film template includes a scored portion and wherein the scored portion is forced by the compliant balloon to separate from the outer surface of the film template and protrude outwardly from the outer surface of the film template when the compliant balloon is in the inflated configuration, and wherein the separated scored portion forms an aperture in the film template.

* * * * *